(12) United States Patent
Dressler et al.

(10) Patent No.: US 11,969,360 B2
(45) Date of Patent: Apr. 30, 2024

(54) SURGICAL INSTRUMENT SYSTEM FOR TOTAL KNEE REPLACEMENT WITH FORCE SENSOR ADAPTERS AND FORCE SENSOR SYSTEMS

(71) Applicant: DEPUY SYNTHES PRODUCTS, INC., Raynham, MA (US)

(72) Inventors: Matthew R. Dressler, Fort Wayne, IN (US); Jackson R. Heavener, Warsaw, IN (US); Daniel D. Auger, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 246 days.

(21) Appl. No.: 17/480,572

(22) Filed: Sep. 21, 2021

(65) Prior Publication Data

US 2022/0096248 A1     Mar. 31, 2022

Related U.S. Application Data

(60) Provisional application No. 63/085,474, filed on Sep. 30, 2020.

(51) Int. Cl.
| | |
|---|---|
| *A61F 2/46* | (2006.01) |
| *A61B 17/02* | (2006.01) |
| *A61B 17/14* | (2006.01) |
| *A61F 2/38* | (2006.01) |
| *A61F 2/30* | (2006.01) |

(52) U.S. Cl.
CPC .......... *A61F 2/4657* (2013.01); *A61F 2/3859* (2013.01); *A61F 2/389* (2013.01); *A61F 2/461* (2013.01); *A61F 2/4684* (2013.01); *A61B 17/02* (2013.01); *A61B 17/14* (2013.01); *A61F 2002/30604* (2013.01); *A61F 2002/4663* (2013.01); *A61F 2002/4666* (2013.01)

(58) Field of Classification Search
CPC ....................... A61F 2/4657; A61F 2002/4666
See application file for complete search history.

(56) References Cited

U.S. PATENT DOCUMENTS

| | | | | |
|---|---|---|---|---|
| 5,197,488 A | * | 3/1993 | Kovacevic | ................ A61F 2/38 |
| | | | | 600/595 |
| 5,470,354 A | * | 11/1995 | Hershberger | ......... A61F 2/4684 |
| | | | | 600/595 |

(Continued)

OTHER PUBLICATIONS

International Search Report for International Application No. PCT/US2021/071515, dated Dec. 22, 2021, 7 pages.

*Primary Examiner* — Nicholas W Woodall
(74) *Attorney, Agent, or Firm* — Barnes & Thornburg LLP

(57) ABSTRACT

An orthopaedic surgical instrument system includes a sensor adapter and multiple surgical instruments. The sensor adapter includes a housing with a force sensor positioned within the housing and a sensor contact configured to transfer force to the force sensor extending from the housing. Each surgical instrument includes a sensor connector configured to receive the sensor adapter at a predetermined location relative to the surgical instrument. Each sensor adapter further includes a registering feature to engage an anatomical feature of a patient or another surgical instrument. The surgical instruments may include a shim that may be attached to a gap assessment tool or a tibial insert trial. Methods associated with the surgical instrument system are also disclosed.

19 Claims, 30 Drawing Sheets

(56) References Cited

U.S. PATENT DOCUMENTS

| | | | |
|---|---|---|---|
| 5,733,292 | A | 3/1998 | Gustilo et al. |
| 7,195,645 | B2 | 3/2007 | Disilvestro et al. |
| 7,632,283 | B2 * | 12/2009 | Heldreth ................ A61B 5/103 |
| | | | 606/102 |
| 8,926,530 | B2 * | 1/2015 | Stein ...................... A61B 5/686 |
| | | | 600/587 |
| 8,968,412 | B2 * | 3/2015 | Wogoman ............. A61F 2/4684 |
| | | | 623/20.29 |
| 9,248,030 | B2 | 2/2016 | Amirouche |
| 10,206,792 | B2 * | 2/2019 | Sherman ............... A61F 2/4657 |
| 2009/0018544 | A1 | 1/2009 | Heavener |
| 2010/0191068 | A1 | 7/2010 | Bewernitz et al. |
| 2010/0249659 | A1 | 9/2010 | Sherman et al. |
| 2013/0079884 | A1 | 3/2013 | Stein et al. |
| 2016/0310297 | A1 | 10/2016 | Anes et al. |
| 2018/0214283 | A1 | 8/2018 | Johannaber et al. |
| 2019/0059916 | A1 | 2/2019 | Yoo et al. |

* cited by examiner

SURGICAL INSTRUMENT SYSTEM FOR TOTAL KNEE REPLACEMENT WITH FORCE SENSOR ADAPTERS AND FORCE SENSOR SYSTEMS

CROSS-REFERENCE TO RELATED APPLICATIONS

This application claims priority under 35 U.S.C. § 119(e) to U.S. Provisional Patent Application No. 63/085,474, entitled "SURGICAL INSTRUMENT SYSTEM FOR TOTAL KNEE REPLACEMENT WITH REMOVABLE FORCE SENSOR ADAPTER," which was filed on Sep. 30, 2020, which is incorporated by reference in its entirety.

TECHNICAL FIELD

The present disclosure relates generally to orthopaedic instruments for use in the performance of an orthopaedic joint replacement procedure, and more particularly to orthopaedic surgical instruments for use in the performance of a total knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

During a knee replacement surgery, the orthopaedic surgeon typically uses a variety of different orthopaedic surgical instruments such as, for example, cutting blocks, surgical reamers, broaches, drill guides, prosthetic trials, ligament balancers, and other surgical instruments to prepare the patient's bones to receive the knee prosthesis.

From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During such a knee replacement surgery, there is need to balance ligament tension of a patient's joint. For example, in a total knee replacement procedure, ligament balancing may be performed to ensure a generally rectangular shaped extension gap and a generally rectangular shaped flexion gap at a predetermined joint force value between the patient's natural or prosthetic proximal tibia and the patient's natural or prosthetic distal femur. Surgical instruments generally known as knee distractors or ligament balancers may be inserted between the proximal end of the tibia and the distal end of the femur and operated to space the tibia from the femur to set the orientation and joint space of the knee joint. During operation, a ligament balancer may be used to help balance the surrounding soft tissue (i.e., ligaments) of a patient's joint.

SUMMARY

According to one aspect of the disclosure, a surgical instrument system for an orthopaedic surgical procedure includes a sensor adapter and a plurality of surgical instruments. The sensor adapter includes a housing, a force sensor positioned within the housing, and a sensor contact extending from the housing. The sensor contact is configured to transfer force exerted on the sensor contact to the force sensor. Each of the plurality of surgical instruments includes a sensor connector configured to receive the sensor adapter at a predetermined location relative to the surgical instrument, and a registering feature configured to engage an anatomical feature of a patient or another surgical instrument of the plurality of surgical instruments, wherein the registering feature has a predetermined location relative to the sensor connector.

In an embodiment, when the sensor adapter is coupled to the sensor connector of a first surgical instrument, and when the first surgical instrument is positioned in a surgically prepared knee joint of the patient, the sensor contact is positioned in a predetermined location relative to an anatomical feature of the surgically prepared knee joint.

In an embodiment, when the sensor adapter is coupled to the sensor connector of a first surgical instrument, and when the first surgical instrument is positioned in a surgically prepared knee joint of the patient, the sensor contact is positioned in a predetermined compartment of the surgically prepared knee joint. In an embodiment, the predetermined compartment comprises a medial compartment or a lateral compartment. In an embodiment, the predetermined compartment comprises an anterior compartment or a posterior compartment.

In an embodiment, the housing of the sensor adapter has a first surface, a second surface positioned opposite the first surface, and a perimeter wall extending between the first surface and the second surface. The sensor contact extends from the first surface of the housing. In an embodiment, the sensor contact has a predetermined location on the first surface relative to the perimeter wall.

In an embodiment, the sensor connector of each surgical instrument includes a passageway defined in an outer wall of the surgical instrument, the passageway sized to receive the housing of the sensor adapter; an inner wall extending inward from the outer wall into the passageway, the inner wall configured to confront the first surface or the second surface of the sensor adapter; and a locating feature positioned within the passageway, wherein the locating feature is configured to engage the perimeter wall of the sensor adapter. In an embodiment, the inner wall of a first surgical instrument is configured to confront the first surface, and wherein the inner wall of the first surgical instrument is configured to engage the sensor contact. In an embodiment, the first surgical instrument further includes a second inner wall extending inward from the outer wall into the passageway, the second inner wall configured to engage the second surface of the housing. In an embodiment, the inner wall of a first surgical instrument is configured to confront the second surface and to engage the second surface.

In an embodiment, a first surgical instrument of the plurality of surgical instruments comprises a shim block, and wherein the registering feature of the first surgical instrument includes a lug hole defined through the shim block. In an embodiment, the lug hole is configured to receive a lug of a gap assessment tool handle. In an embodiment, the gap assessment tool handle includes a spacer block, and wherein the spacer block comprises a tibial conforming surface configured to engage a surgically prepared tibia of the patient. In an embodiment, the lug hole is configured to receive a lug of a tibial trial component. In an embodiment, the tibial trial component is configured to engage a proximal surface of a tibial base trial.

In an embodiment, a first surgical instrument of the plurality of surgical instruments comprises a spacer base. The registering feature of the first surgical instrument comprises a tibial conforming surface configured to engage a surgically prepared tibia of the patient. In an embodiments, the spacer base is attached to a spacer block of a gap assessment tool handle.

In an embodiment, a first surgical instrument of the plurality of surgical instruments comprises a surgical saw, and wherein the registering feature comprises a saw blade of the surgical saw.

In an embodiment, a first surgical instrument of the plurality of surgical instruments comprises a lamina spreader, and wherein the registering feature comprises a jaw of the lamina spreader.

In an embodiment, a first surgical instrument of the plurality of surgical instruments comprises a femoral sizer, and wherein the registering feature comprises a foot of the femoral sizer.

In an embodiment, a first surgical instrument of the plurality of surgical instruments comprises a femoral trial component, and wherein the registering feature comprises a bone-contacting surface of the femoral trial component.

In an embodiment, a first surgical instrument of the plurality of surgical instruments comprises a computer-assisted surgery tensioner, and wherein the registering feature comprises a bone-contacting surface of a distractor plate of the tensioner.

According to another aspect, a sensor system for an orthopaedic surgical procedure includes a substrate, a force sensor coupled to the substrate, and a sensor contact positioned on the substrate. The substrate has a first surface configured to attach to an external surface of an orthopaedic surgical instrument. The substrate includes an adhesive coating on the first surface. The sensor contact is configured to transfer force exerted on the sensor contact to the force sensor.

In an embodiment, the system further includes an alignment guide configured to align the substrate in a predetermined position and a predetermined orientation relative to the external surface of the surgical instrument. In an embodiment, the alignment guide includes an outer perimeter that corresponds to an outer perimeter of the external surface of the surgical instrument. In an embodiment, the alignment guide includes an opening configured to receive a feature extending outward from the external surface of the surgical instrument. In an embodiment, the alignment guide includes a visual marking that corresponds to a feature of the external surface of the surgical instrument. In an embodiment, the alignment guide is selectively coupled to the substrate.

In an embodiment, the substrate comprises a rigid layer. In an embodiment, the substrate comprises a circuit board.

According to another aspect, a method for assembling a sensor system includes attaching a sensor assembly to an external surface of an orthopaedic surgical instrument, wherein the sensor assembly includes a substrate having a first surface configured to attach to the surface of the orthopaedic surgical instrument, a force sensor coupled to the substrate, a sensor contact positioned on the substrate and configured to transfer force exerted on the sensor contact to the force sensor, and an alignment guide configured to align the substrate in a predetermined position and a predetermined orientation relative to the external surface of the surgical instrument; and removing the alignment guide from the sensor assembly while the sensor assembly is attached to the external surface.

In an embodiment, attaching the sensor assembly includes aligning an outer perimeter of the alignment guide to an outer perimeter of the external surface of the surgical instrument. In an embodiment, attaching the sensor assembly includes passing an opening in the alignment guide over a feature extending outward from the external surface of the surgical instrument. In an embodiment, attaching the sensor assembly includes aligning a visual marking of the alignment guide with a feature of the external surface of the surgical instrument. In an embodiment, attaching the sensor assembly includes adhering an adhesive coating of the substrate to the external surface of the surgical instrument.

In an embodiment, the method further includes attaching a second orthopaedic surgical instrument to the external surface of the orthopaedic surgical instrument after removing the alignment guide, wherein the second orthopaedic surgical instrument covers the substrate. In an embodiment, the second orthopaedic surgical instrument is rotatably coupled to the orthopaedic surgical instrument, and wherein attaching the second orthopaedic surgical instrument comprises rotating the second orthopaedic surgical instrument into attachment.

According to another aspect, a surgical instrument system for an orthopaedic surgical procedure includes a surgical instrument and a sensor assembly. The surgical instrument has an external surface including a first visual indicator. The sensor assembly includes a substrate, a force sensor coupled to the substrate, a sensor contact positioned on the substrate and configured to transfer force exerted on the sensor contact to the force sensor, and an alignment guide selectively coupled to the substrate. The substrate has a first surface configured to attach to the external surface of the surgical instrument. The substrate includes an adhesive coating on the first surface. The alignment guide includes a second visual indicator that corresponds to the first visual indicator of the surgical instrument. In an embodiment, when the first visual indicator and the second visual indicator are aligned and the sensor assembly is attached to the external surface of the surgical instrument, the substrate is aligned in a predetermined position and a predetermined orientation relative to the external surface of the surgical instrument.

In an embodiment, the external surface of the surgical instrument includes a third visual indicator that corresponds to a feature of the alignment guide. In an embodiment, the third visual indicator corresponds to a perimeter of the alignment guide.

In an embodiment, the substrate comprises a rigid layer. In an embodiment, the substrate comprises a circuit board.

According to another aspect, a method for assembling a surgical instrument system includes aligning a first visual indicator positioned on an external surface of an orthopaedic surgical instrument with a second visual indicator of a sensor assembly, wherein the sensor assembly includes a substrate having a first surface configured to attach to the external surface of the orthopaedic surgical instrument, a force sensor coupled to the substrate, a sensor contact positioned on the substrate and configured to transfer force exerted on the sensor contact to the force sensor, and an alignment guide having a second surface, wherein the second visual indicator is positioned on the second surface; attaching the sensor assembly to the external surface of the orthopaedic surgical instrument when the first visual indicator is aligned with the second visual indicator, wherein when the first visual indicator and the second visual indicator are aligned the substrate is aligned in a predetermined position and a predetermined orientation relative to the external surface of the surgical instrument; and removing the alignment guide from the sensor assembly while the sensor assembly is attached to the external surface.

In an embodiment, the method further includes aligning an outer perimeter of the alignment guide with a third visual indicator positioned on the external surface of the orthopaedic surgical instrument. In an embodiment, attaching the sensor assembly includes adhering an adhesive coating of the substrate to the external surface of the surgical instrument.

According to another aspect, a surgical instrument system for an orthopaedic surgical procedure includes an orthopaedic surgical instrument and a sensor assembly. The sensor assembly includes a substrate, a force sensor coupled to the substrate, a sensor contact positioned on the substrate and configured to transfer force exerted on the sensor contact to the force sensor, and an alignment guide selectively coupled to the substrate. The substrate has a first surface configured to attach to an external surface of the orthopaedic surgical instrument. The substrate includes an adhesive coating on the first surface. The orthopaedic surgical instrument includes a sensor compartment defined in the external surface and a cover moveable between a closed position and an open position. The sensor compartment is configured to receive the substrate of the sensor assembly. When the cover is in the open position the sensor compartment is revealed, and when the cover is in the closed position the sensor compartment is closed. In an embodiment, the cover is rotatably coupled to the orthopaedic surgical instrument.

In an embodiment, the orthopaedic surgical instrument includes an inner wall extending inward from the external surface to an end wall. The inner wall and the end wall cooperate to define the sensor compartment.

In an embodiment, the substrate comprises a rigid layer. In an embodiment, the substrate comprises a circuit board.

According to another aspect, a method for assembling a surgical instrument system includes moving a cover of an orthopaedic surgical instrument to an open position, wherein when the cover is in the open position, a sensor compartment defined in an external surface of the orthopaedic surgical instrument is accessible; attaching a sensor assembly to the external surface of the orthopaedic surgical instrument within the sensor compartment, wherein the sensor assembly includes a substrate having a first surface configured to attach to the external surface of the orthopaedic surgical instrument, a force sensor coupled to the substrate, a sensor contact positioned on the substrate and configured to transfer force exerted on the sensor contact to the force sensor, and an alignment guide configured to align the substrate in a predetermined position and a predetermined orientation relative to the external surface of the surgical instrument; removing the alignment guide from the sensor assembly while the sensor assembly is attached to the external surface; and moving the cover to a closed position when the alignment guide is removed from the sensor assembly, wherein in the closed position the substrate is covered by the cover.

In an embodiment, attaching the sensor assembly includes attaching the sensor assembly to an end wall positioned in the sensor compartment. The orthopaedic surgical instrument includes an inner wall extending inward from the external surface to the end wall. The inner wall and the end wall cooperate to define the sensor compartment.

In an embodiment, moving the cover to the closed position includes rotating the cover from the open position to the closed position. The cover is rotatably coupled to the orthopaedic surgical instrument. In an embodiment, attaching the sensor assembly includes adhering an adhesive coating of the substrate to the external surface of the surgical instrument.

BRIEF DESCRIPTION OF THE DRAWINGS

The detailed description particularly refers to the following figures, in which.

DETAILED DESCRIPTION OF THE DRAWINGS

Figure 1A:
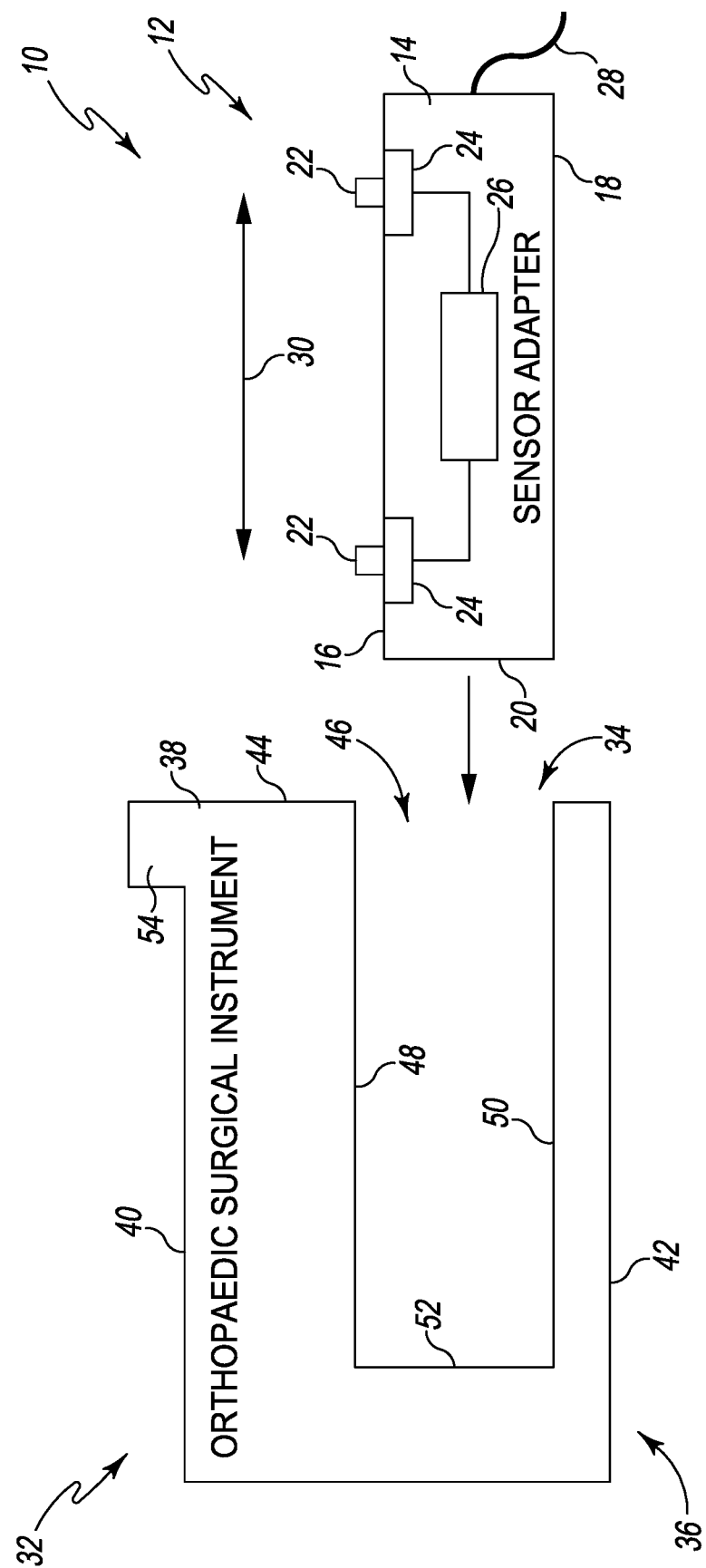
FIGS. 1A-C are a schematic diagrams of a surgical instrument system including a removable force sensor adapter.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1B:
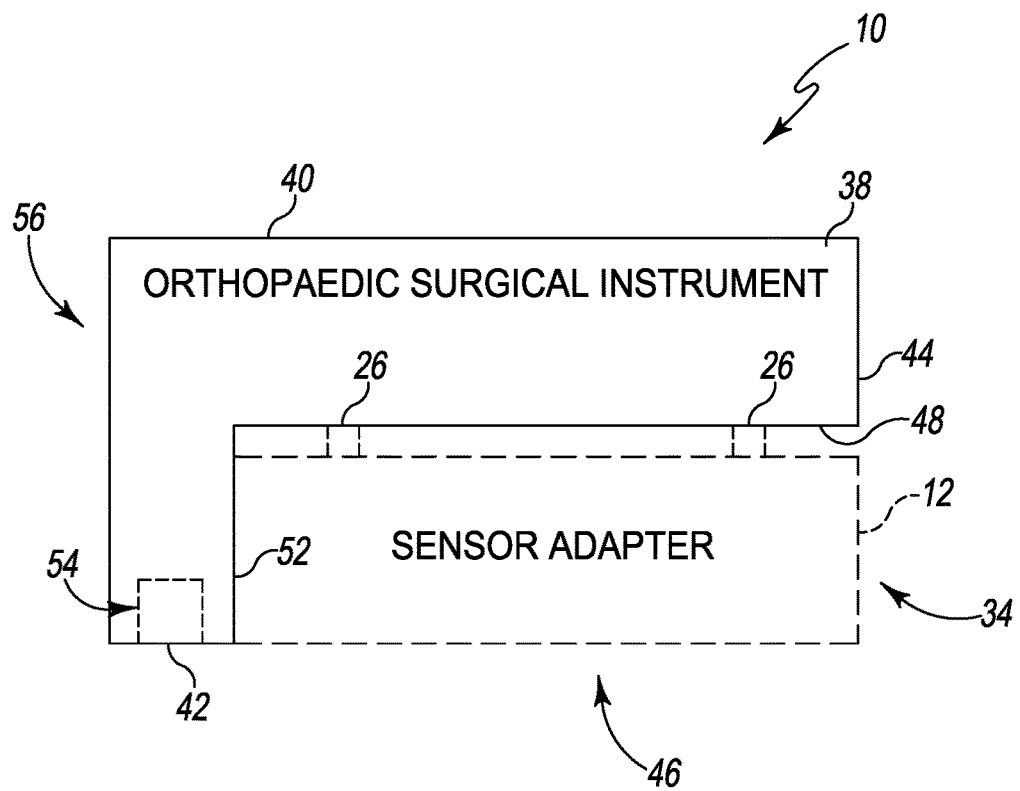
Figure 1C:
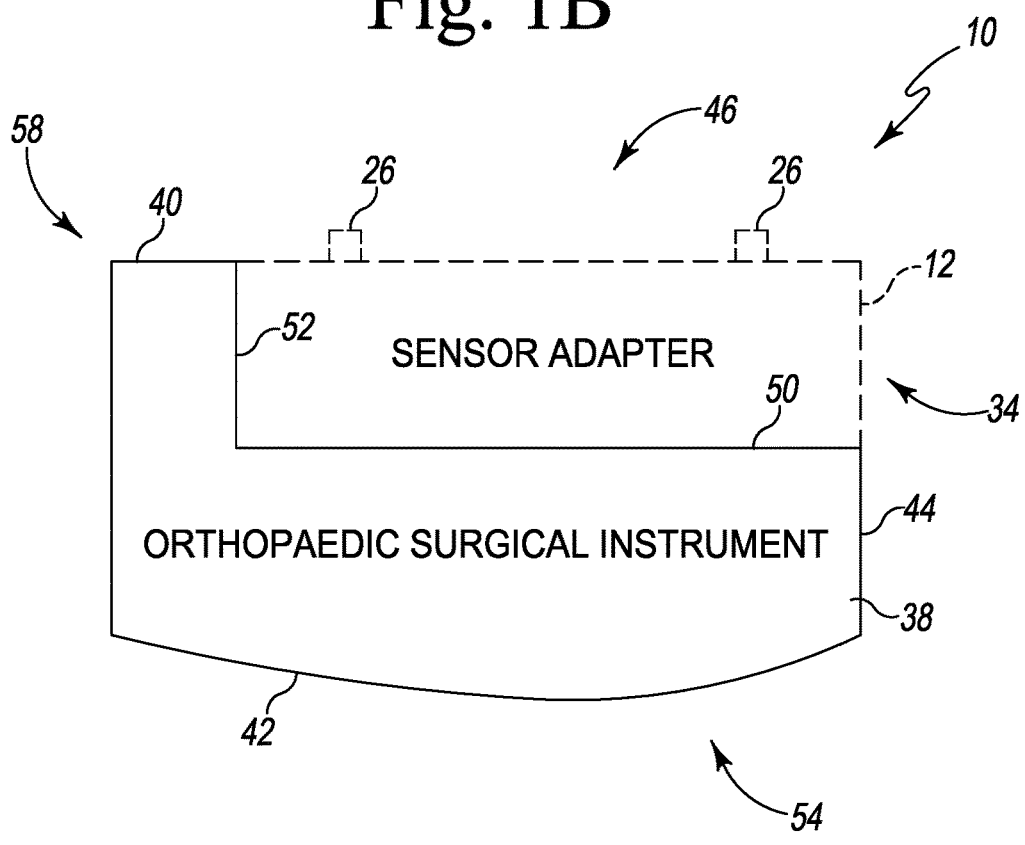

Referring now to FIGS. 1A-C, an orthopaedic surgical instrument system 10 (hereinafter system 10) includes a sensor adapter 12 and multiple surgical instruments 32. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient.

As described further below, the instruments 32 may include surgical saws, gap assessment tools, spacer blocks, shims, balancers, lamina spreaders, femoral sizers, trial components, tensioners, and/or other surgical instruments used in a surgical procedure such as a total knee replacement procedure. Each of the instruments 32 include a sensor connector 34 configured to receive or be coupled to the sensor adapter 12. As such, the sensor adapter 12 may be selectively attached to any of the instruments 32 as described below and used to measure force exerted on the instrument 32 (e.g., by another instrument 32 and/or by the patient's bone). In this way, the sensor adapter 12 may be removed from the instrument 32 and attached to another instrument 32. In some embodiments, the system 10 may include multiple sensor adapters 12, for example with each sensor adapter 12 configured to be attached to a different surgical instrument 32.

The sensor adapter 12 includes a housing 14 that is illustratively molded from a durable polymer such as polyphenylsulfone (PPSU). Alternatively, in other embodiments, the housing 14 may be formed from any resilient polymeric material or may be formed from metallic material. The housing 14 includes an upper surface 16 and a lower surface 18 positioned opposite the upper surface 16. The surfaces 16, 18 may be flat, curved, or otherwise shaped. In some embodiments, the surfaces 16, 18 may be asymmetrical or keyed such that the housing 14 may only be attached to a surgical instrument 32 in a particular predetermined orientation. It should be understood that the terms "upper" and "lower" with regard to the surfaces 16, 18 are for illustrative purposes only, and the sensor adapter 12 may be used in any appropriate orientation relative to a patient's anatomy.

The housing 14 further includes a perimeter surface 20 that extends between the surfaces 16, 18. The perimeter surface 20 may be flat, curved, or otherwise shaped. As described further below, when the sensor adapter 12 is attached to a surgical instrument 32, the perimeter surface 20 may be received and/or retained by a corresponding feature of that surgical instrument 32. In some embodiments, the perimeter surface 20 may be asymmetrical or keyed such that the housing may only be attached to a surgical instrument 32 in a particular predetermined orientation. It should be understood that in some embodiments, the perimeter surface 20 may not extend completely around the housing 14 (e.g., when one or more of the surfaces 16, 18 are curved and contact each other).

The sensor adapter 12 further includes multiple sensor contacts 22 that extend outwardly from the upper surface 16. The sensor contacts 22 may be formed from an elastomeric material, a resilient polymeric material, a metallic material, or other material with known mechanical properties (e.g., stiffness). Each sensor contact 22 is configured to transfer force exerted on the sensor contact 22 to a corresponding sensor pad 24 of the sensor adapter 12. Each sensor pad 24 transfers force exerted on the sensor contact pad 24 to a force sensor 26 positioned within the housing 14 of the sensor adapter 12. The force sensor 26 may be embodied as any electronic force sensor, pressure sensor, or other sensor capable of measuring compression, such as a piezoelectric sensor, capacitive sensor, load cell, or other force sensor. Additionally, although shown as including a single force sensor 26 and multiple contact pads 24, it should be understood that the sensor adapter 12 may include a different number and/or arrangement of sensors 26 and/or contact pads 24. For example, in some embodiments, the sensor adapter 12 may include a sensor 26 coupled to each contact pad 24 and/or each contact pad 24 may include an integrated sensor 26.

A cable 28, which extends from the housing 14, may connect the force sensor 26 to one or more external devices, such as a computer, a display, an external interface device, a transceiver, or other devices. The external device may be used to view, store, or otherwise process force data generated by the force sensor 26. Alternatively, in some embodiments, the sensor adapter 12 may include a wireless communication circuit to communicate with external devices.

The sensor contacts 22 (and thus also the associated contact pads 24) are arranged in a predetermined pattern on the upper surface 16 of the sensor adapter 12. Illustratively, the sensor contacts 22 are arranged linearly and are separated by a predetermined distance 30. In other embodiments, the sensor contacts 22 may be distributed across the upper surface 16 in multiple directions. As described further below, such a distribution of sensor contacts 22 may allow the sensor adapter 12 to measure forces experienced across multiple compartments of the patient's joint (e.g., medial/lateral, anterior/posterior, or otherwise across the joint). Additionally, although illustrated as part of the sensor adapter 12, in some embodiments, sensor contacts 22 may be included in each surgical instrument 32, such that when the sensor adapter 12 is attached to the surgical instrument 32, the sensor contacts 22 transmit force to the sensor pads 24 of the sensor adapter 12.

Each surgical instrument 32 includes a body 38, which may be formed from a resilient polymeric material, a metallic material, or other suitable material. The body 38 includes an upper surface 40, a lower surface 42, and an outer wall 44 extending between the surfaces 40, 42. Each of the surfaces 40, 42 may be flat, curved, or otherwise shaped. For example, the instruments 36, 56 include flat surfaces 40, 42, and the instrument 58 includes a flat surface 40 and a curved surface 42. Similar to the surfaces 16, 18 of the sensor adapter 12, it should be understood that the terms "upper" and "lower" with regard to the surfaces 40, 42 are for illustrative purposes only, and that each surgical instrument 32 may be used in any appropriate orientation relative to a patient's anatomy.

Each surgical instrument 32 includes a sensor connector 34 shaped and configured to receive, or otherwise be coupled to, the sensor adapter 12 to facilitate attachment of the sensor adapter 12 to the corresponding surgical instrument 32. In the illustrative embodiment of FIG. FIGS. 1A-C, each sensor connector 34 is embodied as a passageway, aperture, or slot 46 defined in the outer wall 44 of each surgical instrument 32. It should be understood that each sensor connector 34 may be embodied as any feature configured to receive and/or retain a sensor adapter in a predetermined, unique position and/or orientation relative to the surgical instrument 32. In some embodiments, each surgical instrument may include multiple sensor connectors 34, each configured to receive a sensor adapter 12.

As shown, a ceiling 48 and/or a floor 50 may extend inwardly from the outer wall 44 into the passageway 46. For example, the instrument 36 includes a floor 50 and a ceiling 48 extending inwardly from the slot 46, the instrument 52 includes a ceiling 48 extending inwardly from the passageway 46, and the instrument 56 includes a floor 50 extending inwardly from the passageway 46. The passageway 46, the floor 50, and/or the ceiling 48 are configured to receive the sensor adapter 12. For example, the passageway 46 (and thus the floor 50 and/or ceiling 48) may be asymmetrically shaped or otherwise keyed to receive the surfaces 16, 18 of the sensor adapter 12. In particular, each ceiling 48 may be shaped to confront the upper surface 16, and each floor 50 may be shaped to confront and/or engage the lower surface 18. Thus, in some embodiments, the sensor adapter 12 may only be inserted into the instrument 32 in a particular predetermined orientation. Of course, in other embodiments, each sensor connector 34 of each surgical instrument 32 may be embodied as a different connector or feature capable of receiving or coupling to the sensor adapter 12 such as a passageway, a trough, a recess, a guide feature, a railing, snaps, a magnetic connector, or any other feature capable of coupling the orthopaedic surgical instruments 36, 56, 58 with the sensor adapter 12.

As shown, the sensor connector 34 of each instrument 32 further includes a locating feature 52 positioned within the passageway 46. The locating feature 52 is illustrated in FIGS. 1A-C as an end wall 52, and is configured to engage the perimeter wall 20 of the sensor adapter 12. When the sensor adapter 12 is fully inserted into the passageway 46 of the instrument 32, the perimeter wall 20 of the sensor adapter 12 engages the locating feature 52. Thus, when the sensor adapter 12 is retained by the locating feature 52, the sensor contacts 22 are located in a predetermined position relative to the locating feature 52. Further, although illustrated as an end wall 52, it should be understood that the locating feature 52 may be embodied as any tab, slot, detent, marking, or other feature configured to position the sensor adapter 12 in a predetermined location relative to the surgical instrument 32. Additionally, in some embodiments the locating feature 52 may also include one or more retaining features such as retaining springs, locking tabs, clips, adhesives, or other features configured to retain the sensor adapter 12 in the predetermined position relative to the locating feature 52.

Each instrument 32 may also include one or more registering features 54. Each of the registering features 54 positions the surgical instrument 32 relative to the patient's anatomy or to another surgical instrument. For example, the registering features 54 may include a tibial conforming surface, a femoral conforming surface, or any other surface configured to contact a surgically prepared bone or other part of the patient's anatomy. As another example, the registering features 54 may include lugs, lug holes, locator tabs, or other features used to attach instruments 32 together into instrument assemblies. Thus, the registering features 54 combined with the locating features 52 may position the sensor adapter 12 (and thus the sensor contacts 22) at a predetermined location relative to the patient's anatomy and/or relative to another surgical instrument (which in turn may be located at a predetermined location relative to the patient's anatomy).

As an illustrative example, the registering feature 54 of the instrument 36 is a tab extending outwardly from the surface 40, which may be received by a corresponding slot or other aperture of another surgical instrument. As another example, the registering feature 54 of the instrument 56 is a lug hole extending inwardly from the surface 42, which may receive a lug of another surgical instrument. As yet another example, the registering feature 54 of the instrument 58 is the surface 42, which has a curved profile that may engage another surgical instrument and/or an anatomical feature of the patient.

As shown in FIGS. 1A-C, the sensor adapter 12 may be attached to each of the instruments 32. As an illustrative example, when the sensor adapter 12 is inserted in the instrument 36, the sensor contacts 22 engage the ceiling 48 of the instrument 36, and the lower surface 18 engages the floor 50 of the instrument 36. Compressive forces experienced by the surfaces 40, 42 of the instrument 36 may be transferred to the force sensor 26 via the sensor contacts 22 and the lower surface 18. The body 38 of the instrument 36 may flex or otherwise deflect a small amount (for example, a few tenths of a millimeter) in order to allow compressive forces to transfer to the sensor adapter 12. In some embodiments, the instrument 36 may include a hinge, a relief, or other flexible component to allow such deflection. In some embodiments, multiple parts of the body 38 may deflect independently such that force may be transferred separately to each of the sensor contacts 22.

When the sensor adapter 12 is attached to the instrument 56, the sensor contacts 22 engage the ceiling 48 of the instrument 56. The lower surface 18 of the sensor adapter 12 is exposed, for example through the passageway 46 or through another opening defined in the lower surface 42. For example, the passageway 46 may be a recess defined in the lower surface 42 and sized to receive the perimeter surface 20 of the sensor adapter 12. Compressive forces may be transferred to the force sensor 26 from the upper surface 40 of the instrument 56 via the sensor contacts 22 and from the lower surface 18 of the sensor adapter 12.

Similarly, when the sensor adapter 12 is attached to the instrument 58, the lower surface 18 engages the floor 50 of the instrument 58. The sensor contacts 22 positioned on the upper surface 16 are exposed, for example through the passageway 46 or through another opening defined in the upper surface 40. For example, the passageway 46 may be a recess defined in the upper surface 40 and sized to receive the perimeter surface 20 of the sensor adapter 12. Compressive forces may be transferred to the force sensor 26 from the sensor contacts 22 and from the lower surface 42 through the instrument 58 to the lower surface 18 of the sensor adapter 12.

Figure 2:
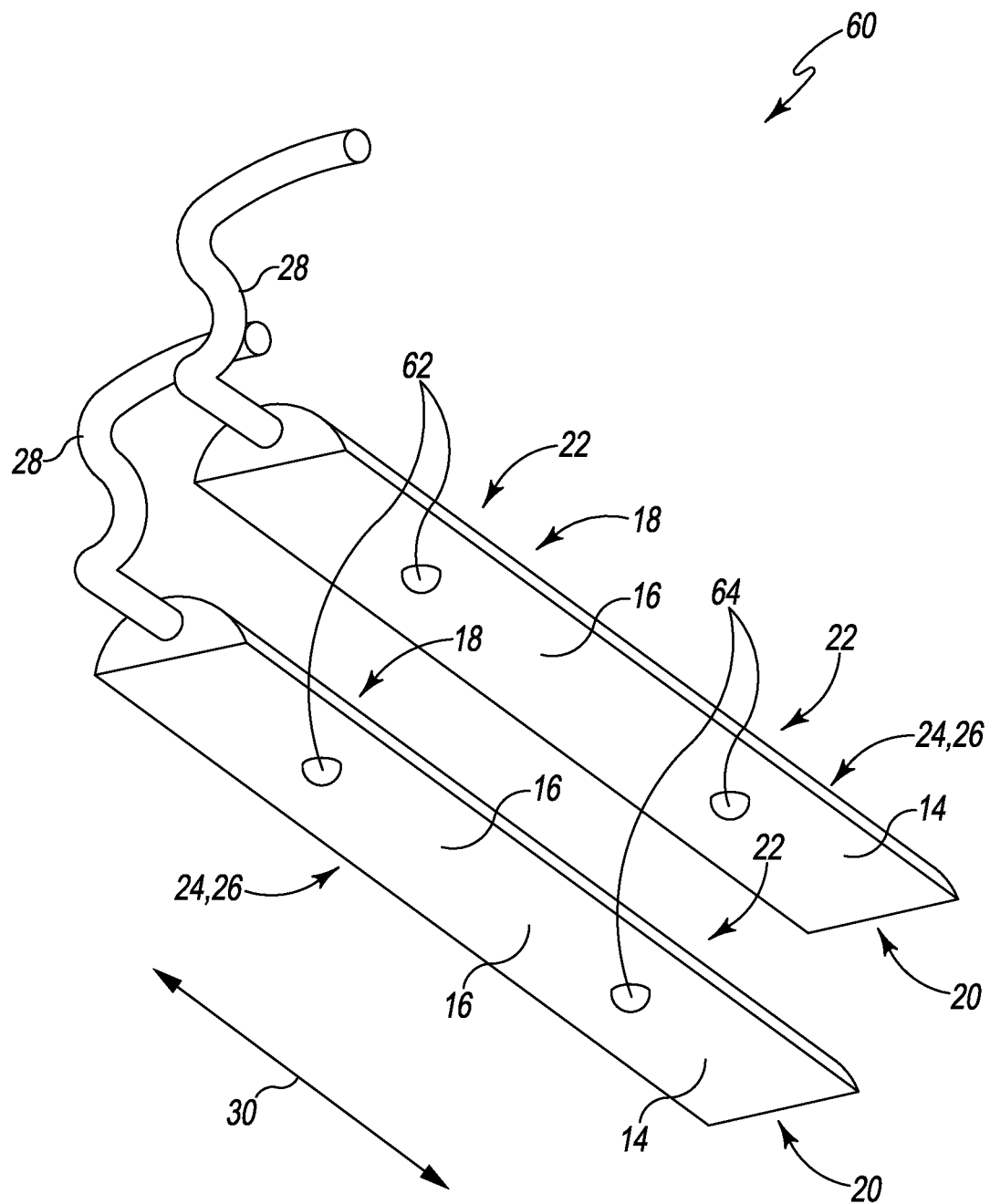
FIG. 2 is a perspective view of an embodiment of a sensor adapter of the system of FIGS. 1A-C.

Referring now to FIG. 2, in the illustrative embodiment, a sensor adapter 60 is embodied as a pair of sensor adapters 12 that may be received by respective sensor connectors 34 of a surgical instrument 32. As shown, each sensor adapter 12 includes a housing 14 having an upper surface 16, a lower surface 18 positioned opposite the upper surface 16, and a perimeter surface 20 that extends between the surfaces 16, 18. As shown, the surface 16 is flat and the surface 18 is curved. In the illustrative embodiment, each housing 14 may thus be inserted into a keyed slot 46 or other keyed sensor connector 34 of each surgical instrument 32, ensuring that the surfaces 16, 18 are arranged in a predetermined orientation. As shown, the perimeter surface 20 is flat. As described above, the perimeter surface 20 may be received by a corresponding locating feature 52 (e.g., a flat end wall) within the keyed slot 46 included in each surgical instrument 32 of the instrument system 10. In some embodiments, the housing 14 of each sensor adapter 12 may have a different profile or other shape such that each sensor adapter 12 may be received by a particular predetermined sensor connector 34 of each surgical instrument 32.

Each sensor adapter 12 of the sensor adapter 60 illustratively includes two sensor contacts 22 that extend outwardly from the upper surface 16. As described above, each sensor contact 22 is configured to transfer force exerted on the sensor contact 22 to a corresponding sensor pad 24 of the sensor adapter 12, which in turn transfers the force to a force sensor 26 positioned within each housing 14 of the sensor adapter 12. The illustrative sensor adapter 60 includes a cable 28 extending from each sensor adapter 12. When inserted into the surgical instrument 32, each cable 28 may extend outward from the slot 46.

The sensor contacts 22 (and thus also the associated contact pads 24) are separated by a predetermined distance 30 from each other on the upper surface 16 of the sensor adapter 60. When attached to a surgical instrument 32 and inserted in the patient's joint space, each of the sensor contacts 22 may measure force experienced in a particular compartment of the knee joint. For example, each sensor contact 62 may measure an anterior compartment, and each sensor contact 64 may measure a posterior compartment. Additionally, when inserted in the surgical instrument 32, each of the sensor adapters 12 may be separated by a predetermined distance in a medial-lateral direction. Thus, the sensor adapter 60 may also measure forces in a medial compartment, a lateral compartment, or other combination of compartments.

Referring now to FIGS. 3-11, various surgical instruments 32 of the surgical instrument system 10 are shown. Each surgical instrument 32 may include one or more sensor connectors 34 to receive one or more corresponding sensor adapters 12. Illustratively, each surgical instrument shown in FIGS. 3-11 is configured to receive one or more sensor adapters 12 of the sensor adapter 60 shown in FIG. 2. The same sensor adapter 12 may be attached to each of the instruments 32 shown in FIGS. 3-11, or multiple sensor adapters 12 may be used. As shown in FIGS. 3-11, each of the sensor connectors 34 may include an aperture configured to receive a corresponding sensor adapter 12. Although the sensor connectors 34 are illustrated as including rectangular apertures, it should be understood that in other embodiments, each aperture may be curved, asymmetrical, keyed, or include other features to receive the corresponding sensor adapter 12 in a particular predetermined orientation.

Figure 3:
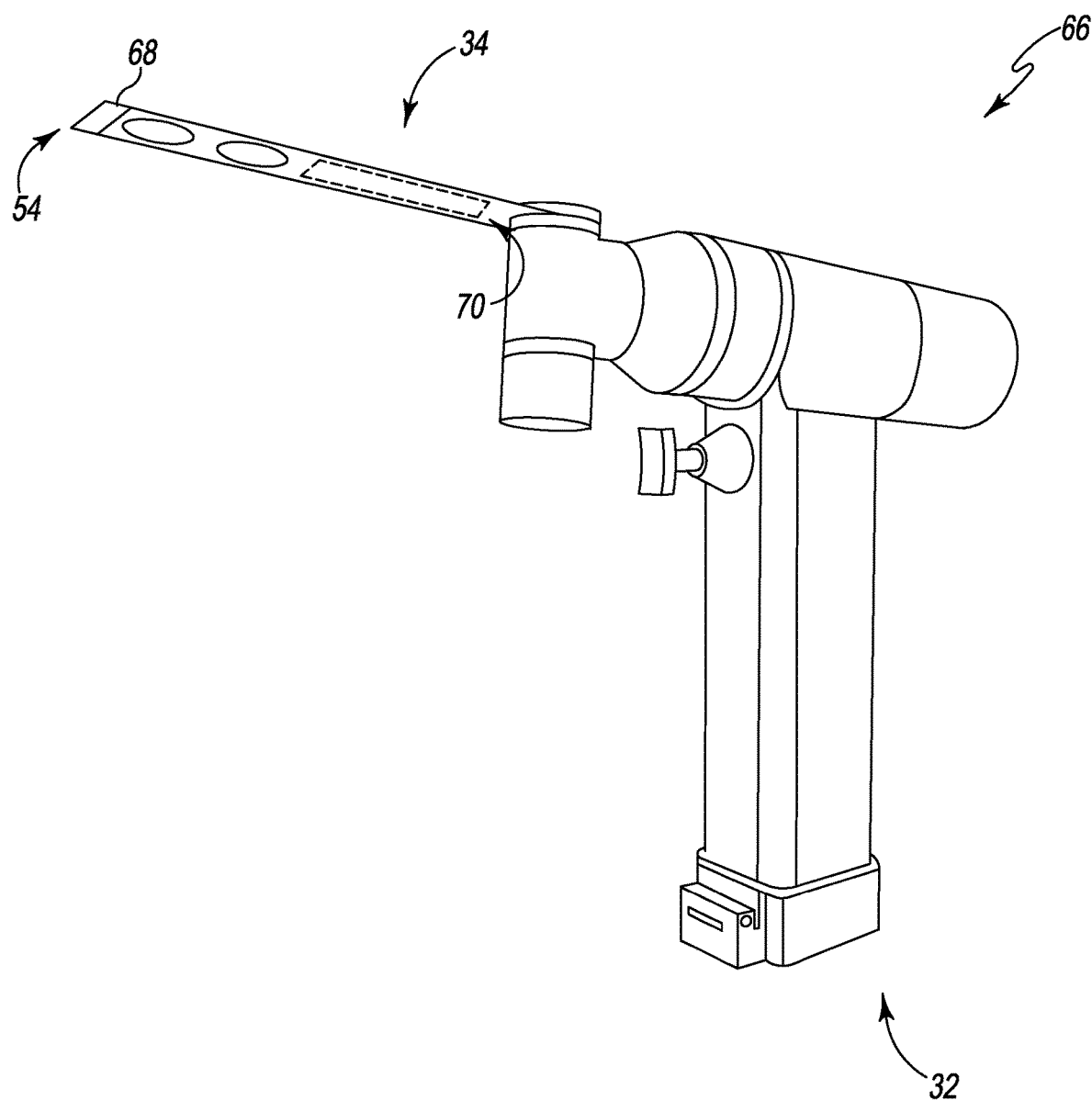
FIG. 3 is a perspective view of an embodiment of a surgical saw including a removable sensor adapter of the system of FIGS. 1A-C.

As shown in FIG. 3, one embodiment of a surgical instrument 32 is a surgical saw 66. The surgical saw 66 includes a saw blade 68. Illustratively, the saw blade 68 of the surgical saw 66 includes a sensor connector 34, which is illustratively embodied as an aperture 70, similar to the passageway 46 of the orthopaedic surgical instruments 36, 56, 58 described above in regard to FIGS. 1A-C. The aperture 70 is configured to receive the sensor adapter 12. As shown, an end of the saw blade 68 may be a registering feature 54. For example, when the saw blade 68 cuts into the patient's tibia to a predetermined depth, the aperture 70 (and thus the attached sensor adapter 12) may be in a predetermined position relative to the patient's knee joint. Additionally or alternatively, the saw blade 68 may be positioned relative to the patient's anatomy using one or more markings, cutting guides, jigs, or other instruments and/or registration features.

Figure 4:
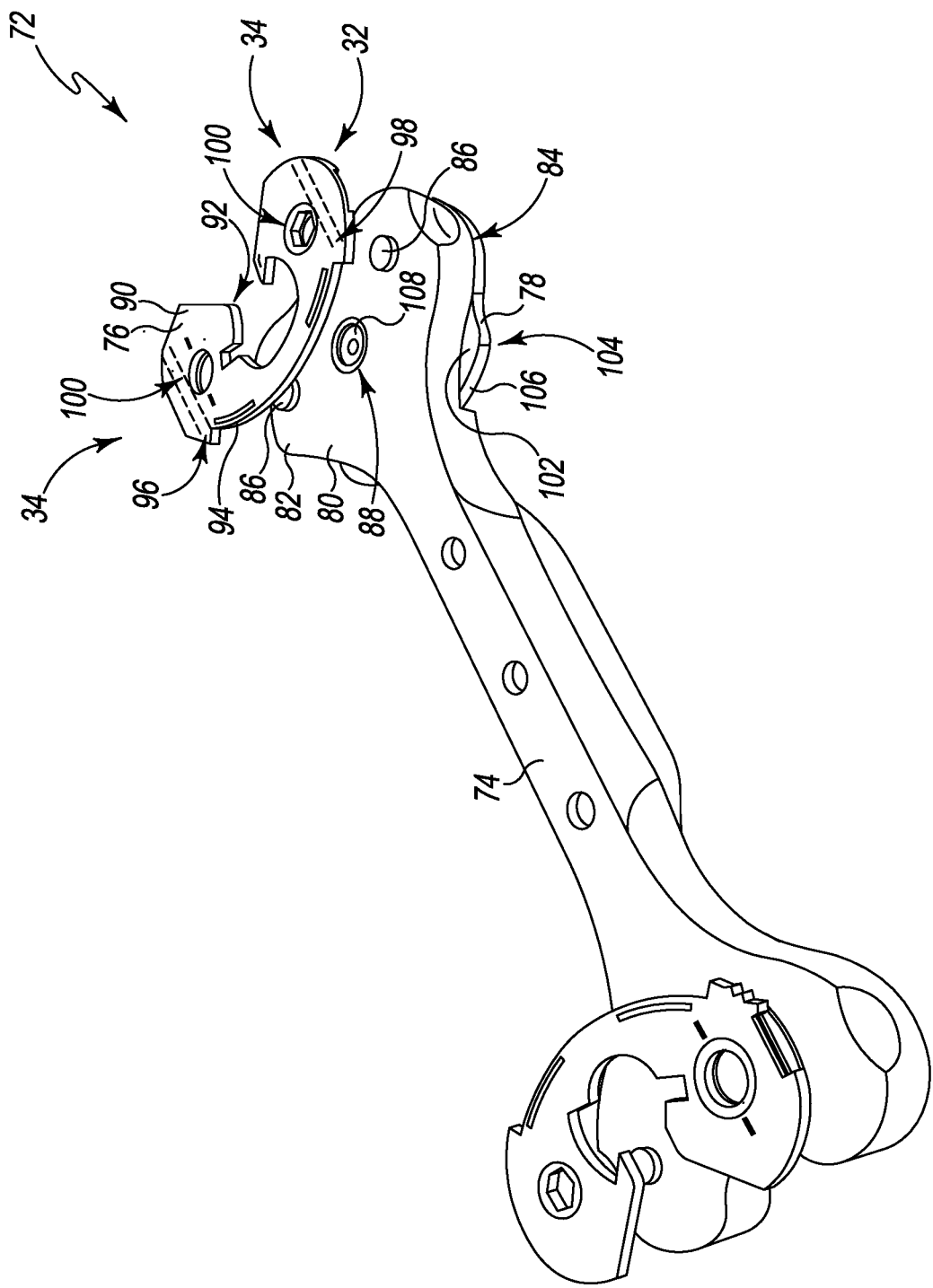
FIG. 4 is a perspective view of an embodiment of a gap assessment tool with a shim that may be attached to a removable sensor adapter of the system of FIGS. 1A-C.

As shown in FIG. 4, another embodiment of a surgical instrument 32 is a gap assessment tool 72. As described further below, a surgeon may use the gap assessment tool 72 in an orthopaedic procedure such as total knee replacement to balance a patient's knee joint. The gap assessment tool 72 is formed as an assembly of an elongated handle 74, a shim 76, and a base 78.

As shown, the elongated handle 74 extends into a paddle-shaped spacer block 80. The spacer block 80 includes a proximal surface 82 and a distal surface 84. A pair of lugs 86 extend proximally from the proximal surface 82. A circular bore 88 extends through the surfaces 82, 84 of the spacer block 80. Although illustrated as including a single spacer block 80, it should be understood that in some embodiments, the gap assessment tool 72 may include spacer blocks 80 on either end of the handle 74. In those embodiments, each spacer block 80 may have a different thickness.

The shim 76 includes a pair of opposing surfaces 90, 92. In some embodiments the surfaces 90, 92 may be reversible. An outer wall 94 extends between the surfaces 90, 92. The shim 76 has a predetermined thickness between the surfaces 90, 92 (i.e., a height of the outer wall 94), such as five millimeters or six millimeters. Illustratively, the shim 76 includes a pair of sensor connectors 34, which are illustratively embodied as keyed slots 96, 98 defined in the outer wall 94. Each slot 96, 98 is similar to the passageway 46 of the orthopaedic surgical instruments 36, 56, 58 described above in regard to FIGS. 1A-C, and is configured to receive a sensor adapter 12 (e.g., a sensor adapter 12 of the sensor adapter 60 of FIG. 2). In an embodiment, the system 10 may include multiple shims 76, each having a different thickness between the surfaces 90, 92.

A pair of lug holes 100 extend through the surfaces 90, 92. Each of the lug holes 100 are sized to receive a corresponding lug 86 of the spacer block 80. Accordingly, each of the lug holes 100 may be a registering feature 54, as the lug holes 100 ensure that the shim 76 is attached to the spacer block 80 at a predetermined position. Each of the lugs 86 and/or lug holes 100 may include one or more retaining features such as spring retainers to retain the shim 76 against the spacer block 80.

The base 78 includes a proximal surface 102 and a distal surface 176. An outer wall 106 extends between the surfaces 102, 104. As described further below, the proximal surface 102 is shaped to match and receive the distal surface 84 of the spacer block 80. In some embodiments, the proximal surface 102 may further include keys or other features that match the spacer block 80 in a particular predetermined orientation. The distal surface 176 may include a tibial conforming surface for contacting a patient's surgically prepared tibia, as described further below. The base 78 further includes a central stud 108 that extends outwardly from the proximal surface 42. The stud 108 fits within the central bore 88 of the spacer block 80. The stud 108 may include a hog ring or other feature to retain the base 78 against the spacer block 80.

Figure 5:
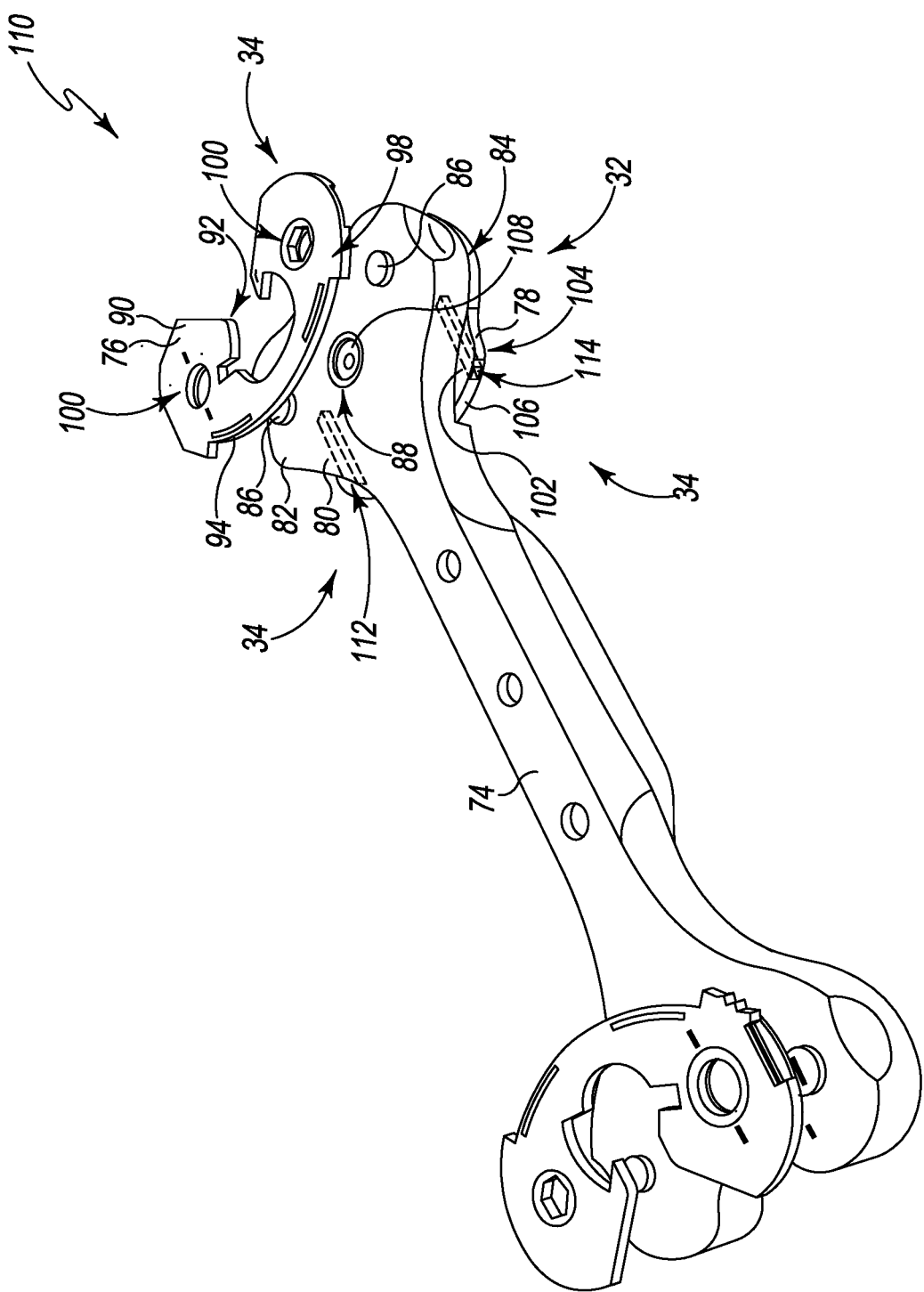
FIG. 5 is a perspective view of an embodiment of a gap assessment tool with a base that may be attached to a removable sensor adapter of the system of FIGS. 1A-C.

Another potential embodiment of a gap assessment tool 110 is shown in FIG. 5. Similar to the gap assessment tool 72 shown in FIG. 4, the gap assessment tool 110 includes an elongated handle 74, a shim 76, and a base 78. As shown in FIG. 5, the base 78 includes a pair of sensor connectors 34, which are illustratively embodied as keyed slots 112, 114 defined in the outer wall 106 of the base 78. Each slot 110, 112 is similar to the passageway 46 of the orthopaedic surgical instruments 36, 56, 58 described above in regard to FIGS. 1A-C, and is configured to receive a sensor adapter 12 (e.g., a sensor adapter 12 of the sensor adapter 60 of FIG. 2).

Figure 6:
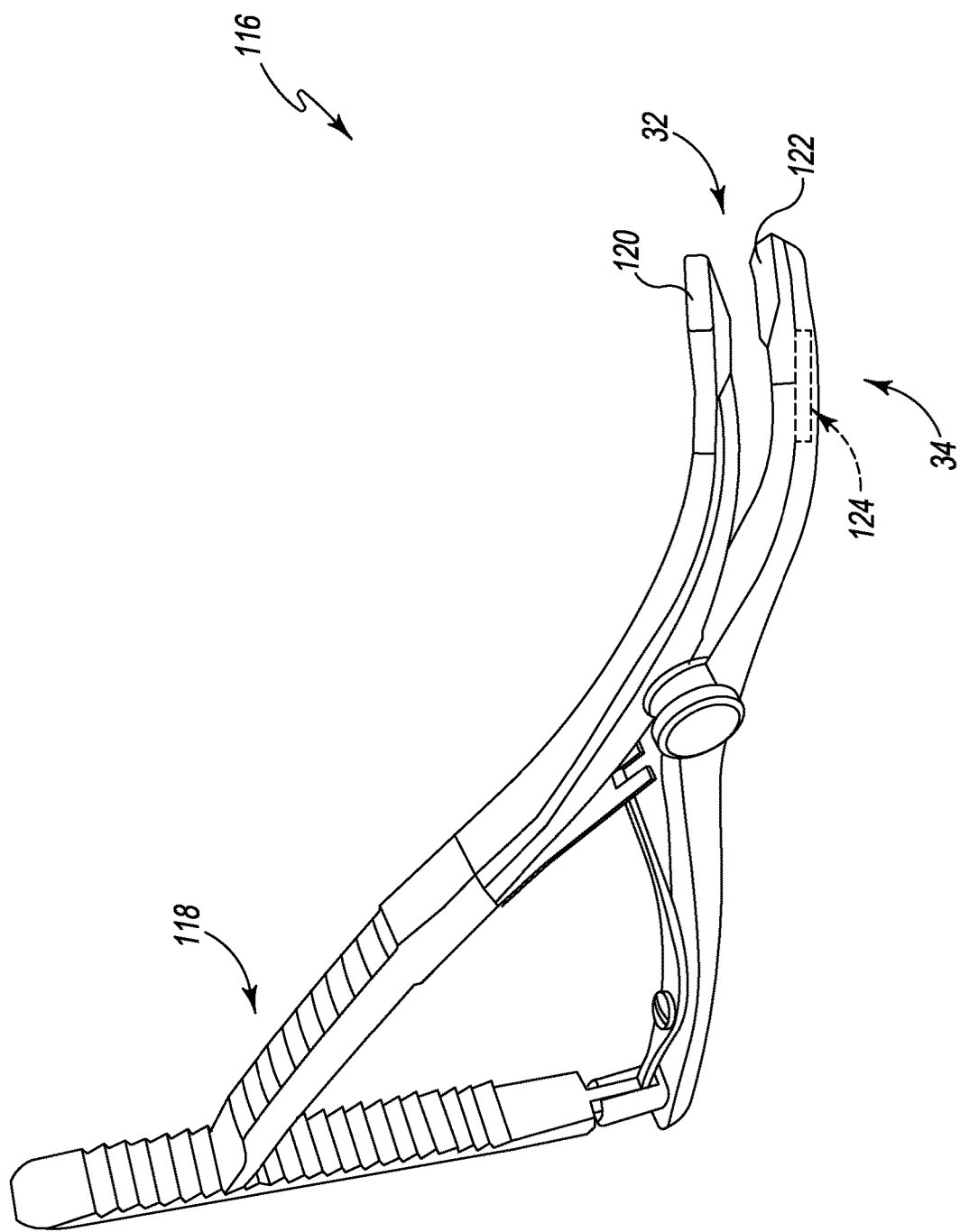
FIG. 6 is a perspective view of an embodiment of a lamina spreader that may be attached to a removable sensor adapter of the system of FIGS. 1A-C.

As shown in FIG. 6, one embodiment of a surgical instrument 32 is a lamina spreader 116. The illustrative lamina spreader 116 includes a handle assembly 118 and a pair of jaws 120, 122. Illustratively, the lower jaw 122 of each lamina spreader 116 includes a sensor connector 34, which is illustratively embodied as a keyed slot 124, similar to the passageway 46 of the orthopaedic surgical instruments 36, 56, 58 described above in regard to FIGS. 1A-C. The slot 124 is configured to receive the sensor adapter 12.

Figure 7:
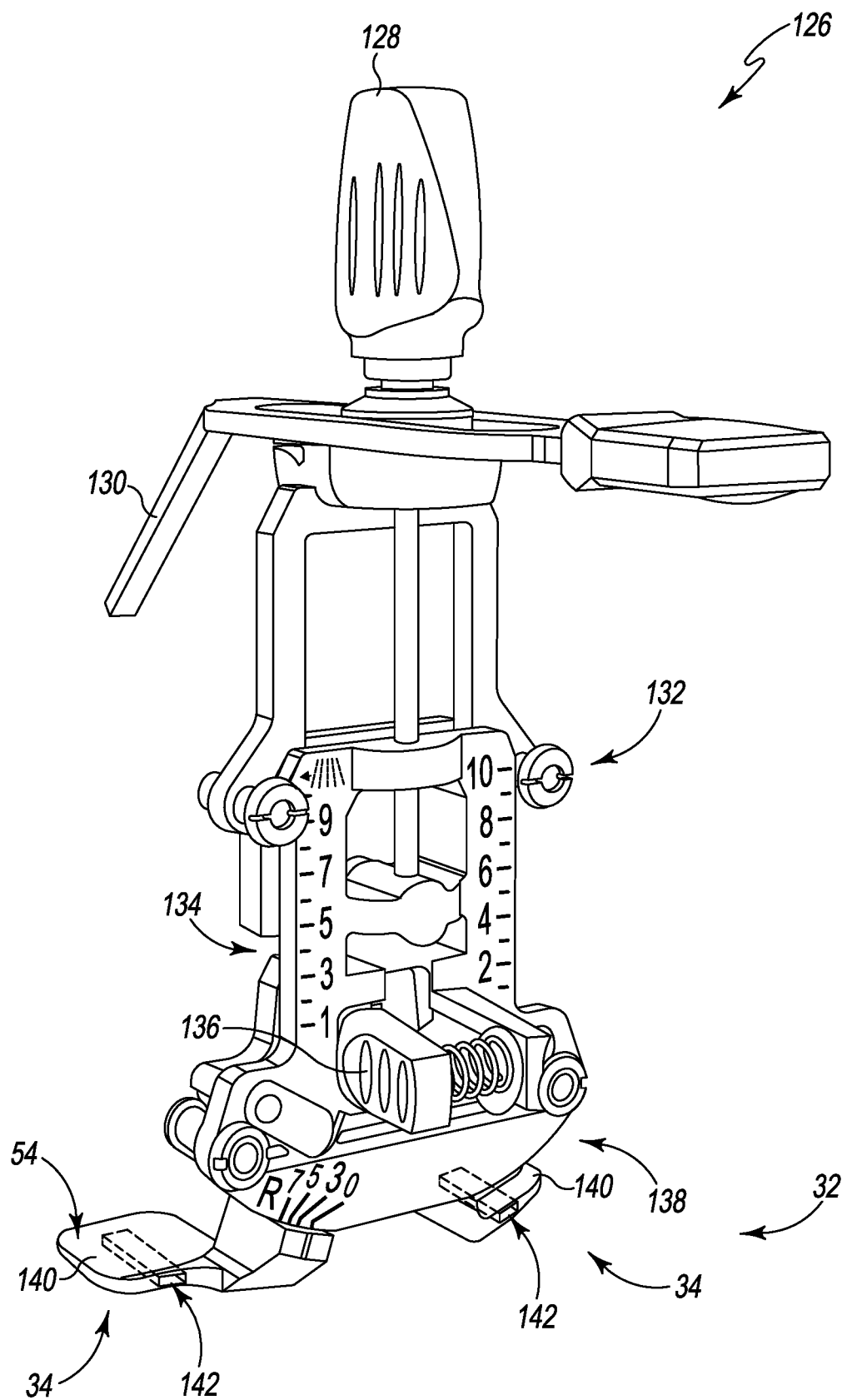
FIG. 7 is a perspective view of an embodiment of a measured femoral sizer that may be attached to a removable sensor adapter of the system of FIGS. 1A-C.

As shown in FIG. 7, one embodiment of a surgical instrument 32 is a measured femoral sizer 126. The measured sizer 126 includes a size locking knob 128 and a stylus 130 that may be configured to contact the patient's anterior femur. The measured sizer 126 further includes multiple pin guide holes 132 which may be used to fix the measured sizer 126 to the patient's distal femur. The measured sizer 126 further includes femoral size markings 134, a femoral rotation lever 136, and rotation markings 138. The measured sizer 126 also includes a pair of feet 140. Illustratively, each foot 140 of the measured sizer 126 includes a sensor connector 34, which is illustratively embodied as a keyed slot 142, similar to the passageway 46 of the orthopaedic surgical instruments 36, 56, 58 described above in regard to FIGS. 1A-C. Each slot 142 is configured to receive the sensor adapter 12. The feet 140 are configured to contact the posterior femur, and thus may be registering features 54 for the measured sizer 126.

Figure 8:
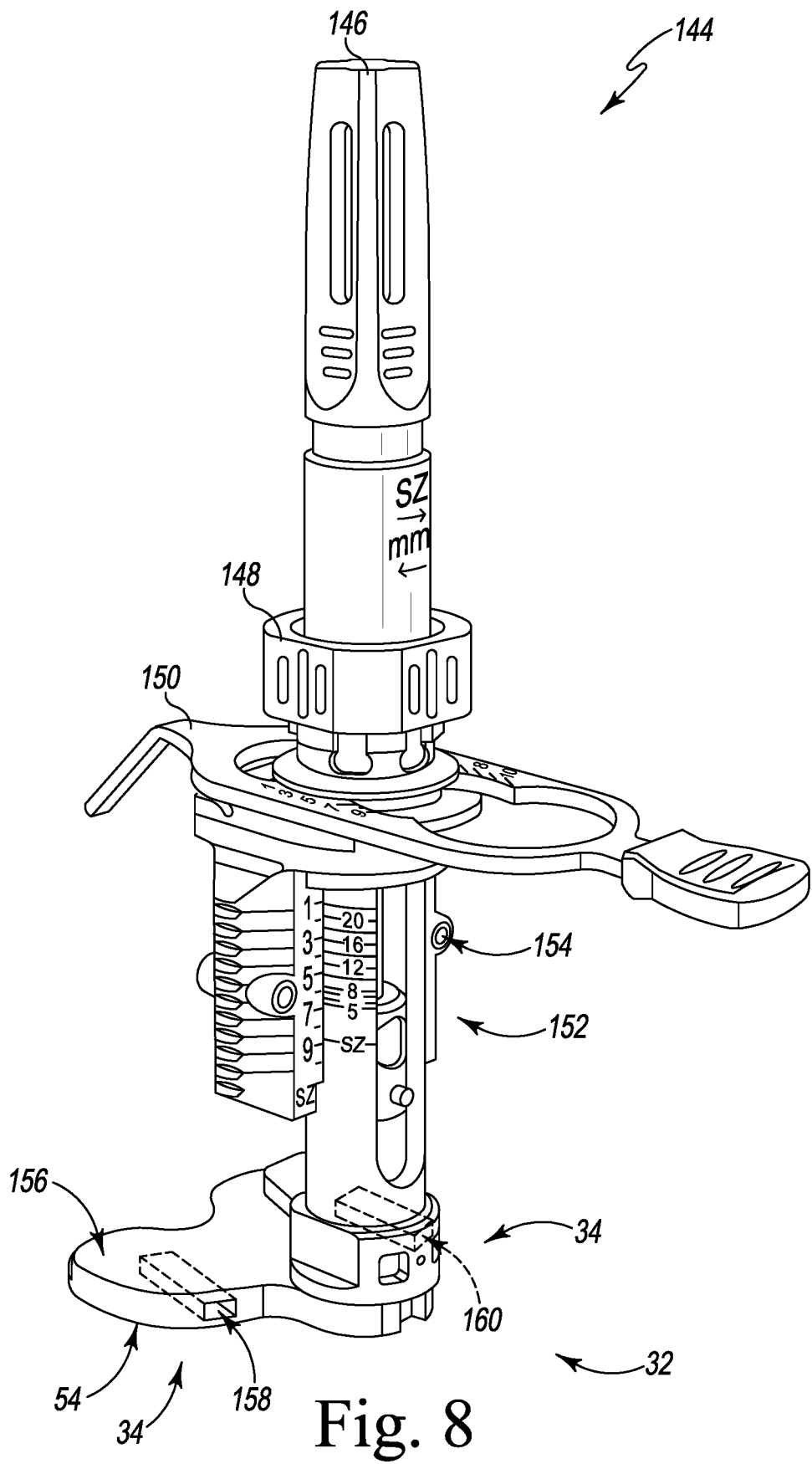
FIG. 8 is a perspective view of an embodiment of a balanced femoral sizer that may be attached to a removable sensor adapter of the system of FIGS. 1A-C.

As shown in FIG. 8, another embodiment of a surgical instrument 32 is a balanced femoral sizer 144. The balanced sizer 144 includes a tensioning knob 146, a locking knob 148, and a stylus 150 that may be configured to contact the patient's anterior femur. The balanced sizer 144 further includes a sizing scale 152 and multiple pin holes 154 which may be used to fix the balanced sizer 144 to the patient's distal femur. The balanced sizer 144 includes a foot 156 having a pair of sensor connectors 34, which are illustratively embodied as keyed slots 158, 160. Each slot 158, 160 is similar to the passageway 46 of the orthopaedic surgical instruments 36, 56, 58 described above in regard to FIGS. 1A-C, and is configured to receive a sensor adapter 12 (e.g., a sensor adapter 12 of the sensor adapter 60 of FIG. 2). The foot 156 is configured to contact the posterior femur and the proximal tibia of the patient, and thus may be a registering feature 54 for the balanced sizer 144.

Figure 9:
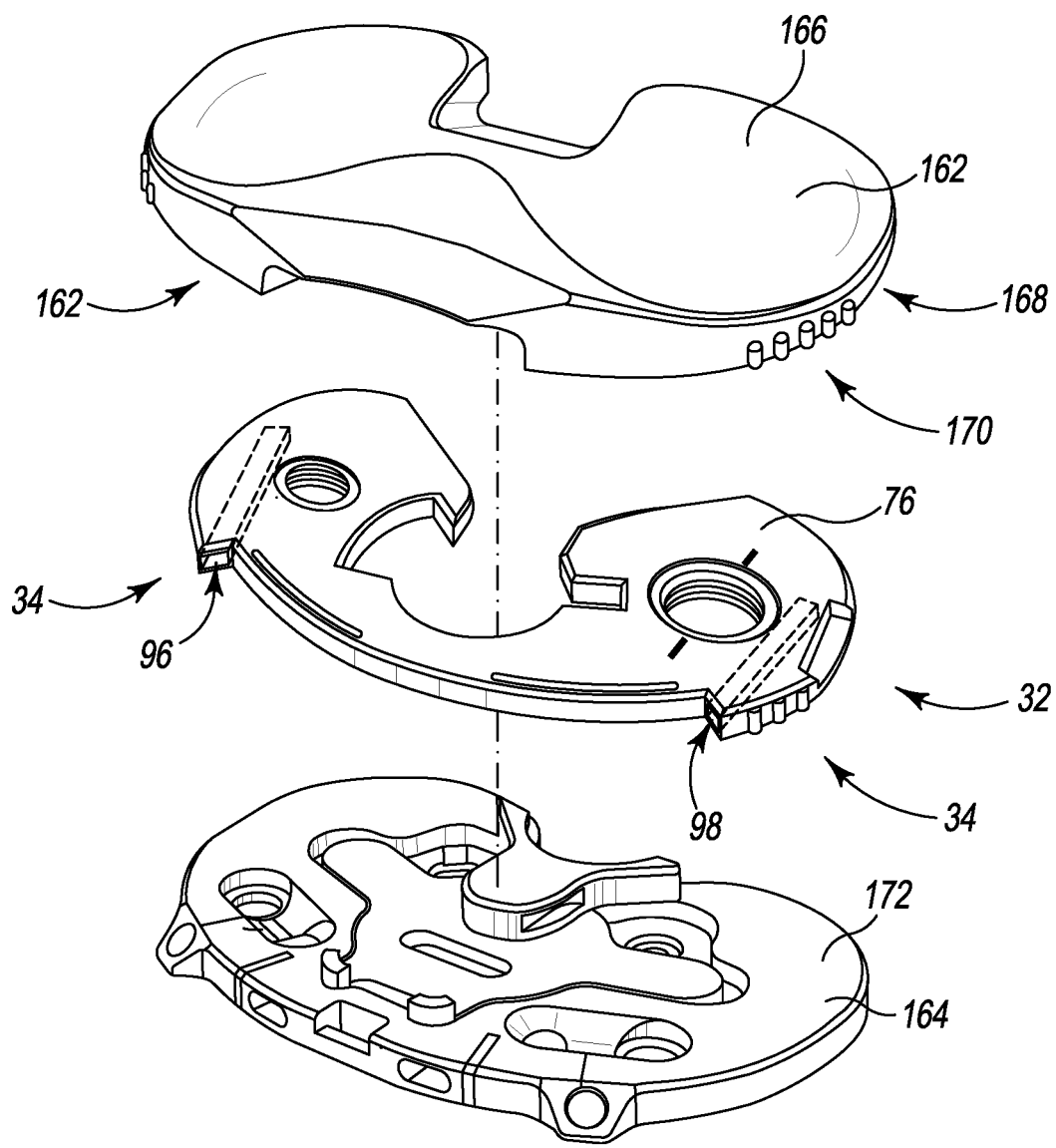
FIG. 9 is a perspective view of an embodiment of a trial component stack with a shim that may be attached to a removable sensor adapter of the system of FIGS. 1A-C.

FIG. 9 shows another embodiment of a surgical instrument 32 included in a trial component stack that may be used during trial reduction of a patient's knee joint. As shown, the trial component stack includes a tibial insert trial 162, a shim 76, and a tibial base trial 164. The insert trial 162 includes an upper, articulation surface 166 and a lower surface 176. As described further below, the articulation surface 166 is profiled to match and receive a femoral trial component, and the lower surface 176 is shaped to match and receive the shim 76. A pair of lugs 170 extend outwardly from the lower surface 176. In some embodiments, the lower surface 176 may include keys or other features that match the shim 76 and/or the tibial base trial 164 in a particular predetermined orientation.

The shim 76 may be the same shim 76 shown in FIG. 4 and described above. As such, the shim 76 includes a pair of sensor connectors 34, which are illustratively embodied as the keyed slots 96, 98 defined in the outer wall 102 and configured to receive the sensor adapters 12. The lug holes 100 of the shim 76 receive the lugs 170 of the insert trial 162 and retain the shim against the insert trial 162, and thus may be a registering feature 54 for the shim 76.

The tibial base trial 164 may be affixed to the patient's surgically prepared tibia. The tibial base trial 164 includes an upper, proximal surface 172 that includes features to match and receive one or more of the surfaces 90, 92 of the shim 76. The tibial base trial 164 is illustratively a fixed bearing trial; in other embodiments, the tibial base trial 164 may be a rotating platform trial or other tibial trial.

Figure 10:
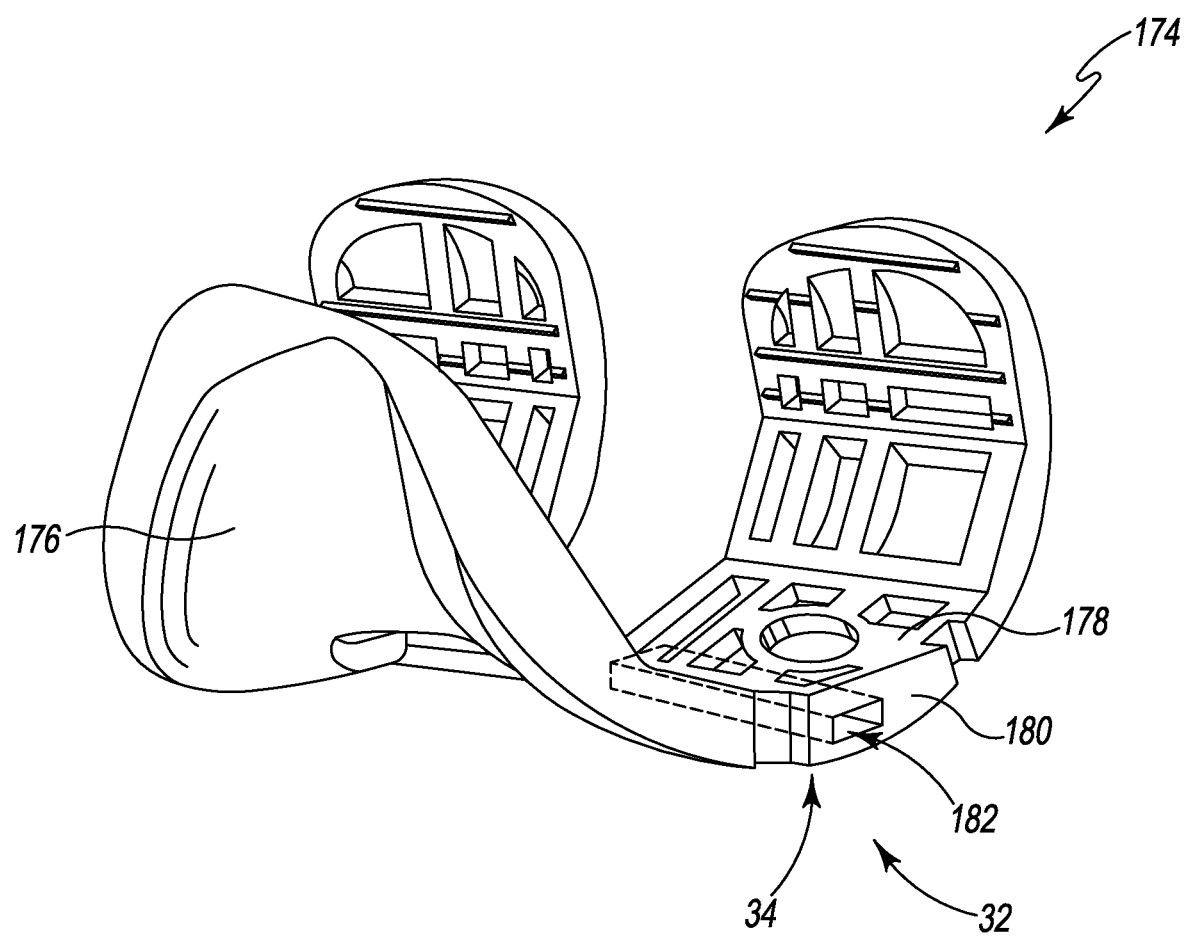
FIG. 10 is a perspective view of an embodiment of a femoral trial component that may be attached to a removable sensor adapter of the system of FIGS. 1A-C.

As shown in FIG. 10, another embodiment of a surgical instrument 32 is a femoral trial component 174. The femoral trial component 174 includes an articulation surface 176 that is profiled to match and receive the articulation surface 166 of the insert trial 162, described above. A bone-facing surface 178 is positioned opposite the articulation surface 176, and a side wall 180 extends between the surfaces 168, 170. Illustratively, the femoral trial component 174 includes a sensor connector 34, which is illustratively embodied as a keyed slot 182 defined in the side wall 180, similar to the passageway 46 of the orthopaedic surgical instruments 36, 56, 58 described above in regard to FIGS. 1A-C. The slot 182 is configured to receive the sensor adapter 12. In some embodiments, the sensor connector 34 may be included in a femoral shim coupled to the bone-facing surface 178 (not shown).

Figure 11:
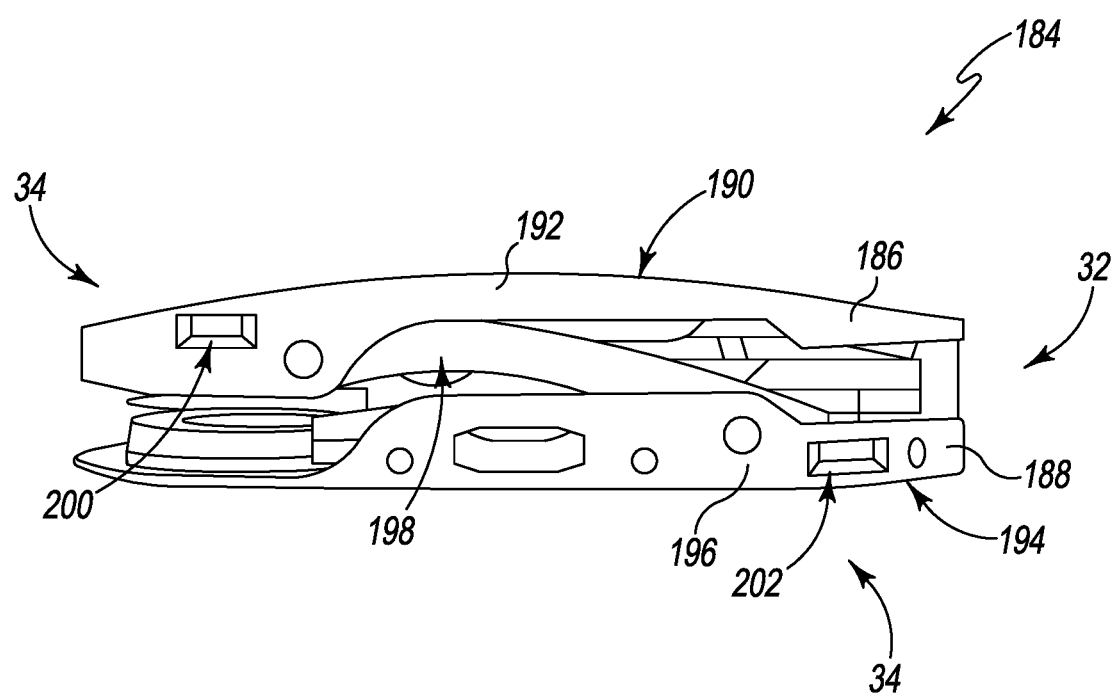
FIG. 11 is a perspective view of an embodiment of a computer-assisted surgery tensioner that may be attached to a removable sensor adapter of the system of FIGS. 1A-C.

As shown in FIG. 11, another embodiment of a surgical instrument 32 is a computer-assisted surgery (CAS) tensioner 184. The illustrative CAS tensioner 184 includes a pair of distractor plates 186, 188. The distractor plate 186 includes a proximal surface 190 surrounded by an outer wall 192, and the distractor plate 188 includes a distal surface 194 surrounded by an outer wall 196. A jacking mechanism 198 is operable to separate the distractor plates 186, 188, thereby applying tension to the patient's joint. Illustratively, the CAS tensioner 184 includes a pair of sensor connectors 34, which are illustratively embodied as keyed slots 200, 202 defined in the outer walls 192, 196, respectively. Each slot 200, 202 is similar to the passageway 46 of the orthopaedic surgical instruments 36, 56, 58 described above in regard to FIGS. 1A-C, and is configured to receive a sensor adapter 12 (e.g., a sensor adapter 12 of the sensor adapter 60 of FIG. 2). Each of the surfaces 190, 194 may be registering features 54.

Figure 12:
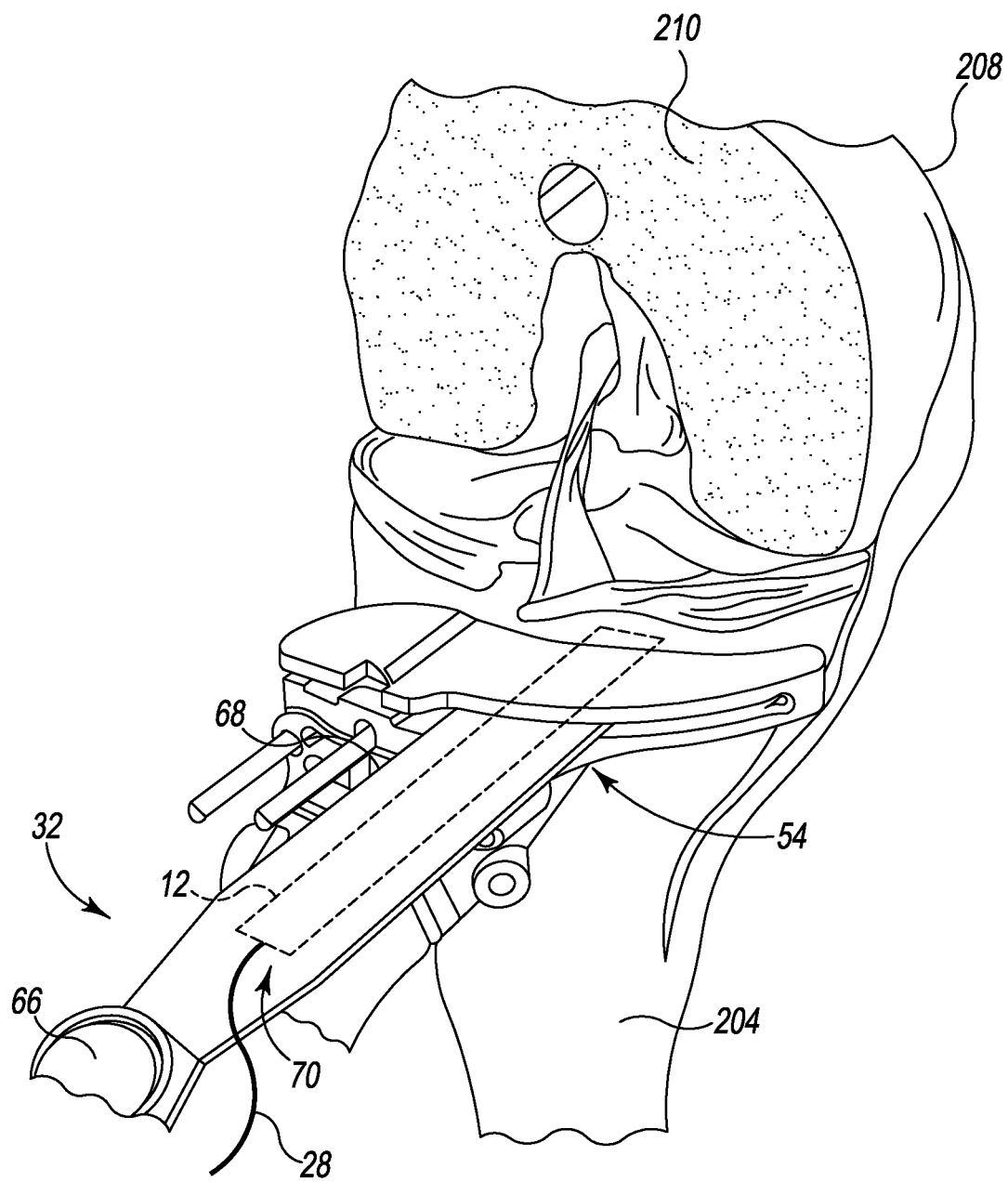
FIGS. 12-18 illustrate an orthopaedic surgical procedure using the surgical instrument system of FIGS. 1A-11.

The surgical instrument system 10 may be utilized during the performance of an orthopaedic surgical procedure similar to that shown in FIGS. 12-18. As shown, a patient's knee joint includes a tibia 204 and a femur 208. A surgeon initially prepares the knee joint, for example by resecting the proximal surface of the patient's tibia 204 with the surgical saw 66. As shown in FIG. 12, the surgeon may attach a sensor adapter 12 to the sensor connector 34 located on the saw blade 68. As shown in FIG. 12, the saw blade 68 may be used with one or more jigs, cutting guides, or other instruments to locate the cut relative to the tibia 204. The surgeon inserts the saw blade 68 into the tibia 204, and when the saw blade 68 completes cutting the tibia 204, the sensor adapter 12 (and thus the sensor contacts 22) are in a predetermined position relative to the tibia 204. The sensor adapter 12 measures forces in the knee joint when inserted in the tibia 204.

Figure 13:
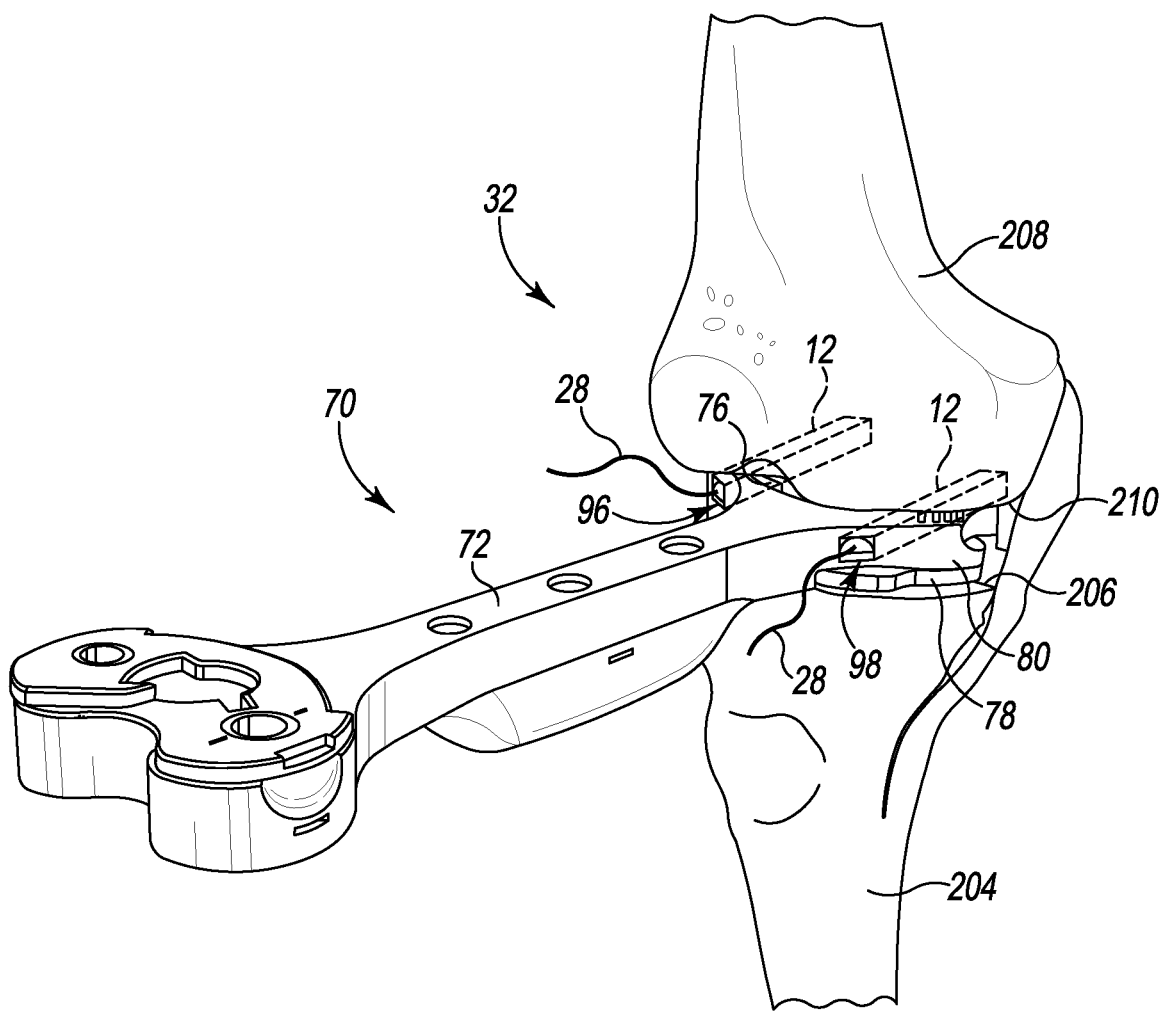
Figure 14:
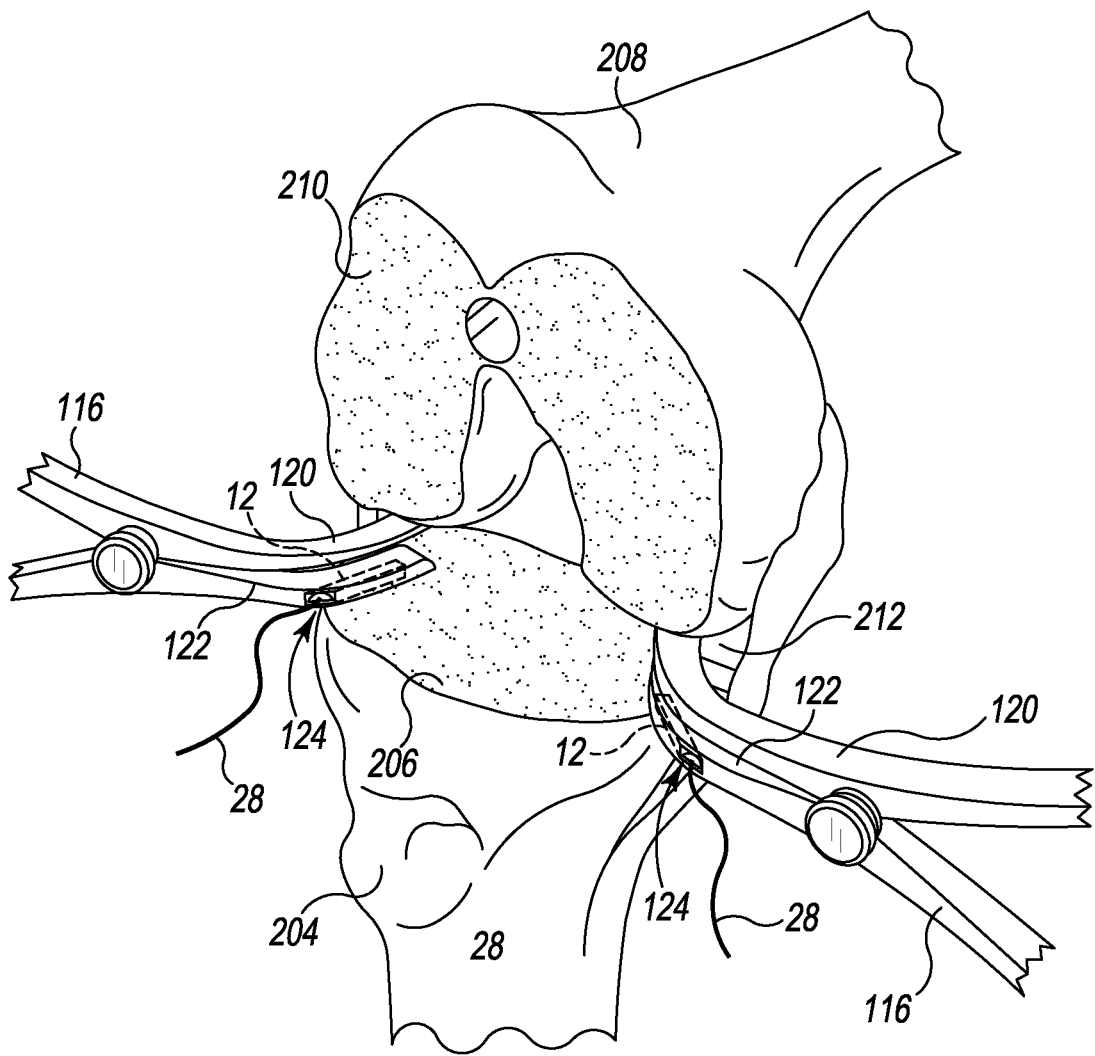

After preparing the tibia 204, a gap is defined between a surgically prepared proximal surface 206 of the tibia and the femur 208. As shown in FIGS. 13-14, the surgeon may assess flexion and extension gaps through the range of motion. The surgeon may attach a pair of sensor adapters 12 (e.g., a divorced platform sensor adapter 60 as shown in FIG. 2) to the sensor connectors 34 included in the shim 76. The surgeon assembles the gap assessment tool 72 by attaching the base 78 to the spacer block 80 by and attaching the shim 76 (including the sensor adapters 12) to the spacer block 80 as described above. With the patient's knee in extension as shown in FIG. 13, the surgeon inserts the gap assessment tool 72 into the gap defined between the femur 208 and the tibia 204. As shown, the shim 76 contacts a distal surface 210 of the femur 208, and the base 78 contacts the resected surface 206 of the tibia 204. The surgeon may use the outline of the distal surface 104 of the base 78 to locate the gap assessment tool 72 within the joint. When inserted in the joint, the sensor contacts 22 of the sensor adapters 12 are located in predetermined positions relative to the joint. In particular, at least one sensor contact 22 may be positioned in each of the anterior-medial compartment, the posterior-medial compartment, the anterior-lateral compartment, and the posterior-lateral compartment of the knee joint.

With the gap assessment tool 72 inserted in the gap, the surgeon may distract the knee joint, for example by selecting a shim 76 of appropriate thickness, by extending one or more jacks to increase the thickness of the gap assessment tool 72, by using an external distractor (not shown), or using other techniques to apply tension to the knee joint. During the surgical procedure, the femur 208 and the tibia 204 exert forces on the shim 76 and the base 78, respectively. Those forces are transferred to the sensor adapters 12, which generate force sensor data indicative of force and/or pressure across the entire knee joint. The surgeon may use the force sensor data to balance the knee joint, for example by balancing medial and lateral forces and/or by balancing anterior and posterior forces. In some embodiments, for example when preparing a fixed bearing implant, the surgeon may use the force sensor data to assess rotational balance of the knee joint while rotating the assembly 10 about the nominal tibial internal-external rotation axis. The surgeon may rotate the assembly 10 until forces within the knee joint are sufficiently balanced. Further, the surgeon may move the knee between extension (shown in FIG. 13) and flexion to dynamically evaluate the forces in the joint throughout the range of motion.

Additionally, although illustrated in FIG. 13 with a gap assessment tool 72 as shown in FIG. 4, it should be understood that in some embodiments the joint may be balanced using the gap assessment tool 110 shown in FIG. 5. In those embodiments, the surgeon attaches the sensor adapters 12 to the sensor connectors 34 included in the base 78 (rather than the shim 76). After assembling the gap assessment tool 110, the surgeon performs the balancing procedure described above.

Additionally or alternatively, the surgeon may perform flexion gap balancing using lamina spreaders 116 as shown in FIG. 14. The surgeon may attach a sensor adapter 12 to the sensor connector 34 included in each of a pair of lamina spreaders 116. With the patient's knee in flexion as shown in FIG. 14, the surgeon inserts the lamina spreaders 116 into the gap defined between the femur 208 and the tibia 204. As shown, the upper jaws 120 of the lamina spreaders 116 contact posterior condyles 212 of the femur 208, and the lower jaws 122 of the lamina spreaders 116 contact the resected surface 206 of the tibia 204. Thus, when inserted in the joint, the sensor contacts 22 of the sensor adapters 12 (attached to the lower jaws 122) are located in predetermined positions relative to the joint. In particular, at least one sensor contact 22 may be positioned in each of the anterior-medial compartment, the posterior-medial compartment, the anterior-lateral compartment, and the posterior-lateral compartment of the knee joint.

With the lamina spreaders 116 inserted in the gap, the surgeon may distract the knee joint, for example by using the handles 118 of the lamina spreaders 116 to apply tension to the knee joint. During the surgical procedure, the femur 208 and the tibia 204 exert forces on the jaws 120, 122 of the lamina spreaders 116, and those forces are transferred to the sensor adapters 12. The sensor adapters 12 generate force sensor data indicative of force and/or pressure across the entire knee joint. The surgeon may use the force sensor data to balance the knee joint, for example by balancing medial and lateral forces and/or by balancing anterior and posterior forces.

Figure 15:
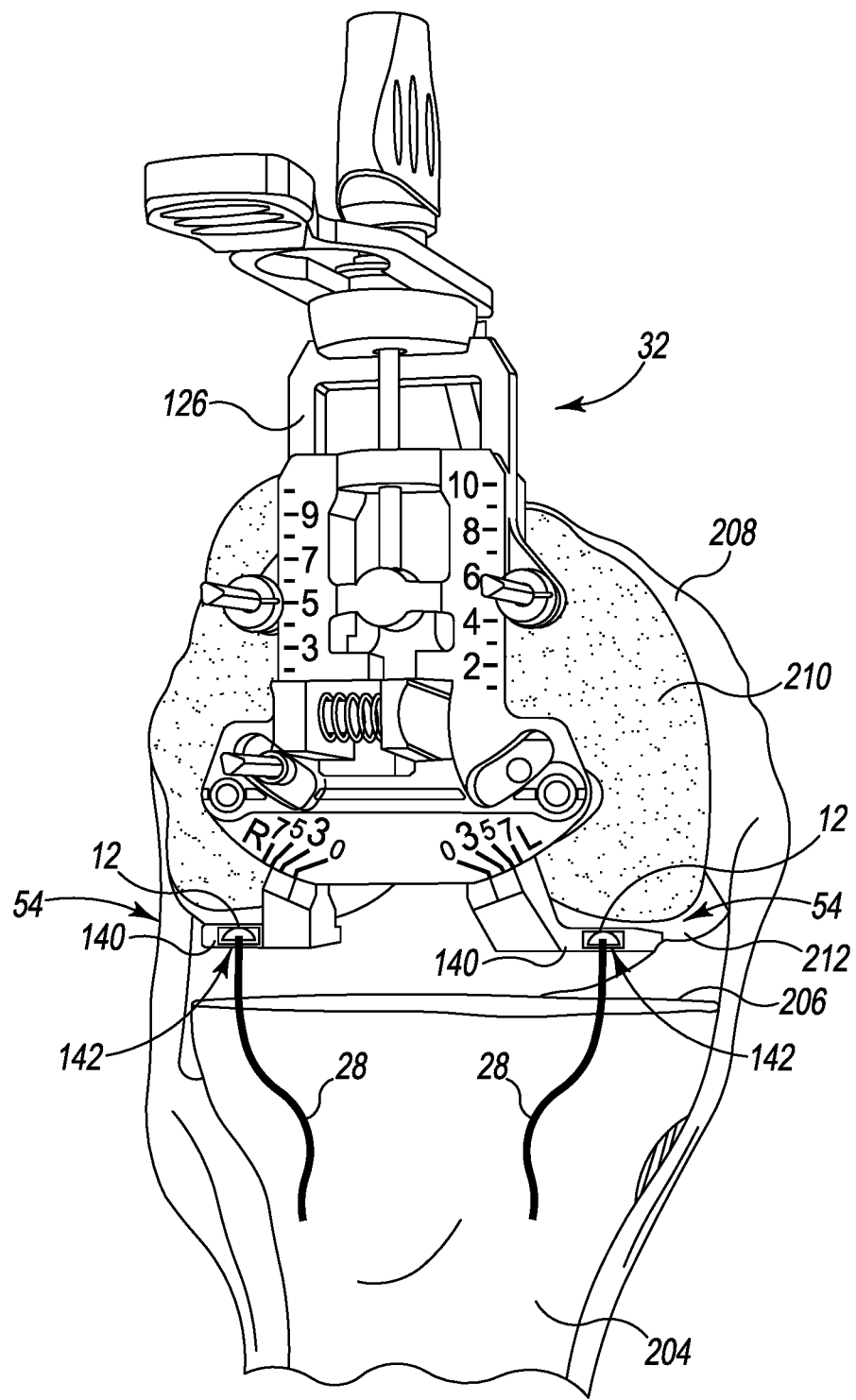

After balancing the knee joint, the surgeon performs femoral sizing and rotation. To perform sizing and rotation, the surgeon may use the measured sizer 126 as shown in FIG. 15 or the balanced sizer 144 shown in FIG. 16. When using the measured sizer 126 as shown in FIG. 15, the surgeon attaches the sensor adapters 12 to the sensor connectors 34 included in the feet 140 of the measured sizer 126. The measured sizer 126 is placed against a resected distal surface 210 of the femur 208 with the feet 140 contacting the posterior condyles 212 of the femur 208. The measured sizer 126 may be secured to the femur 208 with a pin through a fixation hole. The surgeon may squeeze the rotation lever 136 and rotate the measured sizer 126, using the rotation markings 138 to evaluate external femoral rotation with reference to the posterior condyles 212. The surgeon adjusts the superior-inferior position of the stylus 130 to contact the anterior femur 208 at an appropriate point, and uses the size markings 134 to determine proper femoral component sizing. Pins may be inserted into the distal femur 210 through the pin guide holes 132.

During femoral sizing and rotation with the measured sizer 126, the feet 140 are in contact with the posterior condyles 212. The posterior condyles 212 exert forces on the feet 140 which are transferred to the sensor adapters 12. The sensor adapters 12 generate force sensor data indicative of force and/or pressure across the posterior condyles 212, which the surgeon may reference during the surgical procedure.

Figure 16:
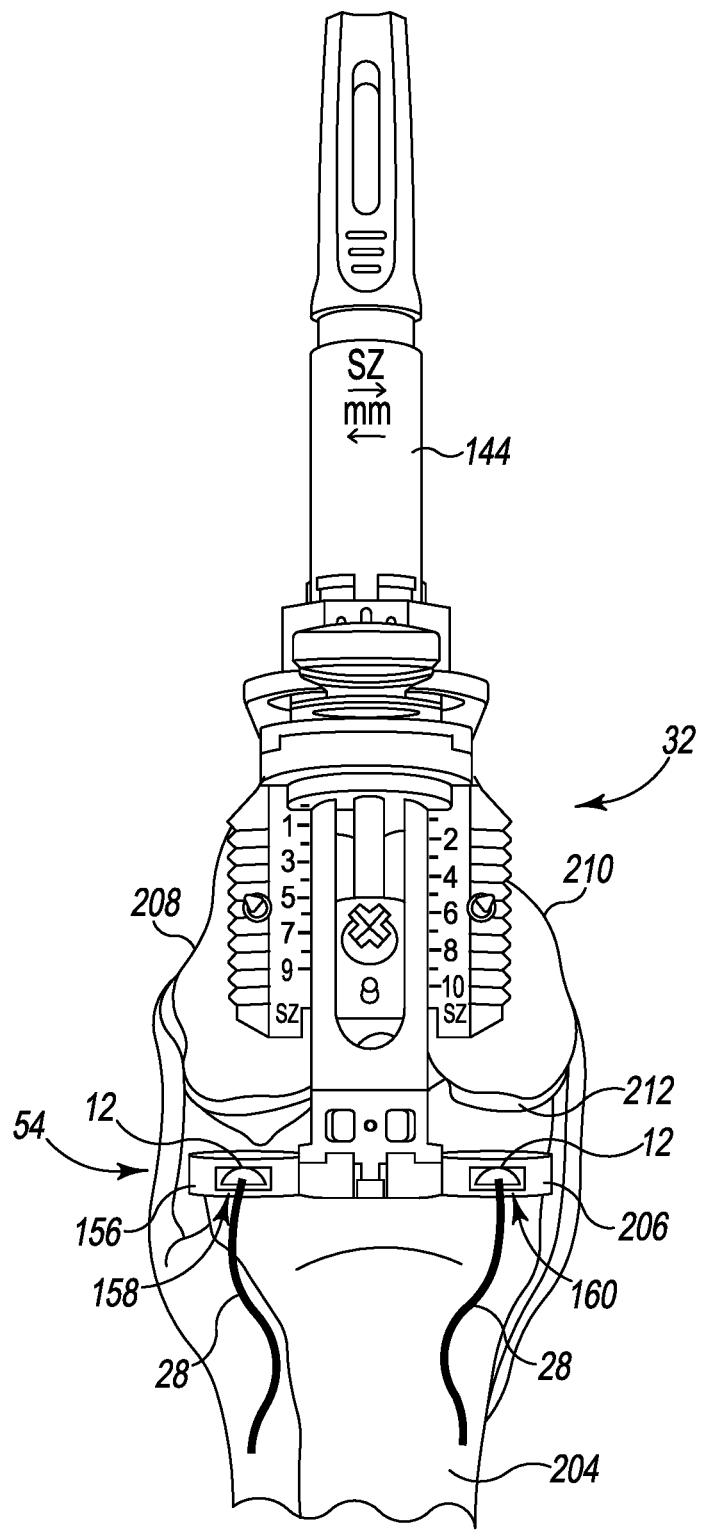

When using the balanced sizer 144 as shown in FIG. 16, the surgeon may select one of multiple feet 156 available to be used with the balanced sizer 144. For example, different feet 156 may be used for cruciate retaining (CR) and posterior stabilized (PS) femoral implants, respectively. The surgeon attaches the sensor adapters 12 to the sensor connectors 34 included in the selected foot 156, and attaches that foot 156 to the balanced sizer 144. The surgeon inserts an intramedullary rod into the intramedullary canal of the patient's femur 208. The surgeon slides the balanced sizer 144 onto the intramedullary rod with the knee joint flexed at 90 degrees. The surgeon rotates the tensioning knob 146 until the foot 156 contacts the posterior condyles 212 of the femur 208. After the foot 156 contacts the posterior condyles 212, the surgeon slides the stylus 150 and sizing scale 152 downward over the balanced sizer 144 until the stylus 150 contacts the anterior femur 208 and the sizing scale 152 contacts the distal femur 210. When in position, the surgeon uses the sizing scale 152 to determine proper femoral component sizing.

After determining femoral sizing, the surgeon rotates the tensioning knob 146 in an opposite direction until the foot 156 contacts the proximal surface 206 of the tibia 204. When contacting the proximal surface 206, the sizing scale 152 may be used to determine proper tibial insert thickness. Additionally, the surgeon may evaluate ligament tension by using the tensioning knob 146 to apply a varus/valgus stress to the knee joint.

During femoral sizing and rotation with the balanced sizer 144, the foot 156 is in contact sequentially with the posterior condyles 212 and then the proximal tibia 206. The posterior condyles 212 and the proximal tibia 206 exert forces on the foot 156 which are transferred to the sensor adapters 12. The sensor adapters 12 generate force sensor data indicative of force and/or pressure across the posterior condyles 212 and the proximal tibia 206, which the surgeon may reference during the surgical procedure.

Figure 17:
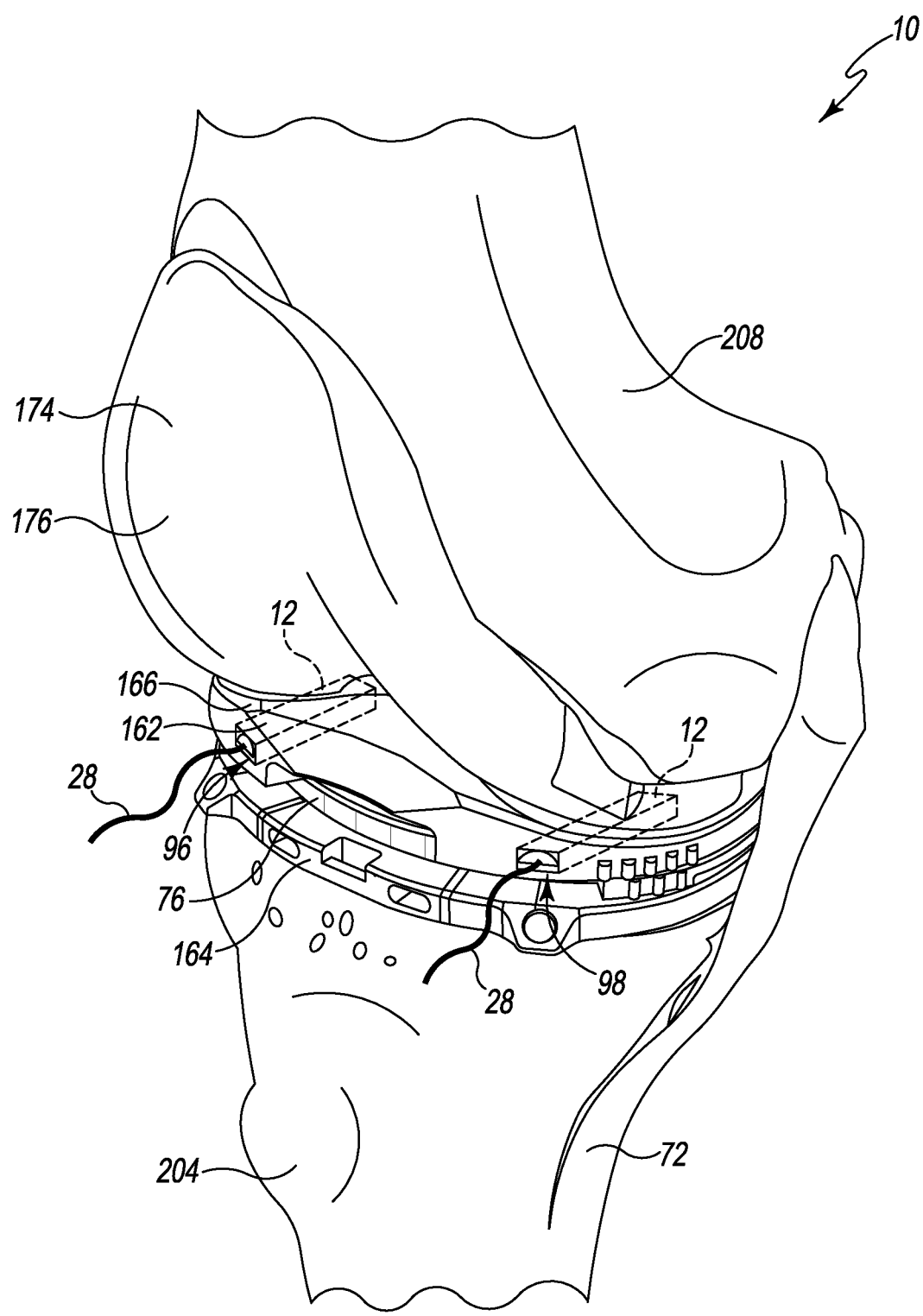

After femoral sizing and rotation, the surgeon may perform a trial reduction of the patient's knee as shown in FIG. 17. After preparing the femur 208, the surgeon inserts the femoral trial component 174 into the surgically prepared femur 208. After preparing the tibia 204, the surgeon inserts the tibial base trial 164 into the surgically prepared tibia 204.

The surgeon selects a shim 76 (which may be the same shim 76 used during soft tissue balancing shown in FIG. 13), and attaches a pair of sensor adapters 12 to the sensor connectors 34 included in the shim 76. The surgeon attaches the shim 76 to the insert trial 162, and then attaches the shim 76 to the tibial base trial 164. As shown, after assembly, the articulation surface 166 of the insert trial 162 engages against the bearing surface 176 of the femoral trial component 174. The surgeon may distract the knee joint, for example by selecting a shim 76 of appropriate thickness, by extending one or more jacks to increase the thickness of the trial stack, by using an external distractor (not shown), or using other techniques to apply tension to the knee joint.

During the surgical procedure, the femur 208 and the tibia 204 (and/or the femoral trial component 174 and the tibial base trial 164) exert forces on the insert trial 162 and the shim 76, respectively. Those forces are transferred to the sensor adapters 12, which generate force sensor data indicative of force and/or pressure across the entire knee joint. The surgeon may use the force sensor data to balance the knee joint, for example by balancing medial and lateral forces and/or by balancing anterior and posterior forces. The surgeon may move the knee joint between extension (shown in FIG. 17) and flexion to dynamically evaluate the forces in the joint throughout the range of motion.

Figure 18:
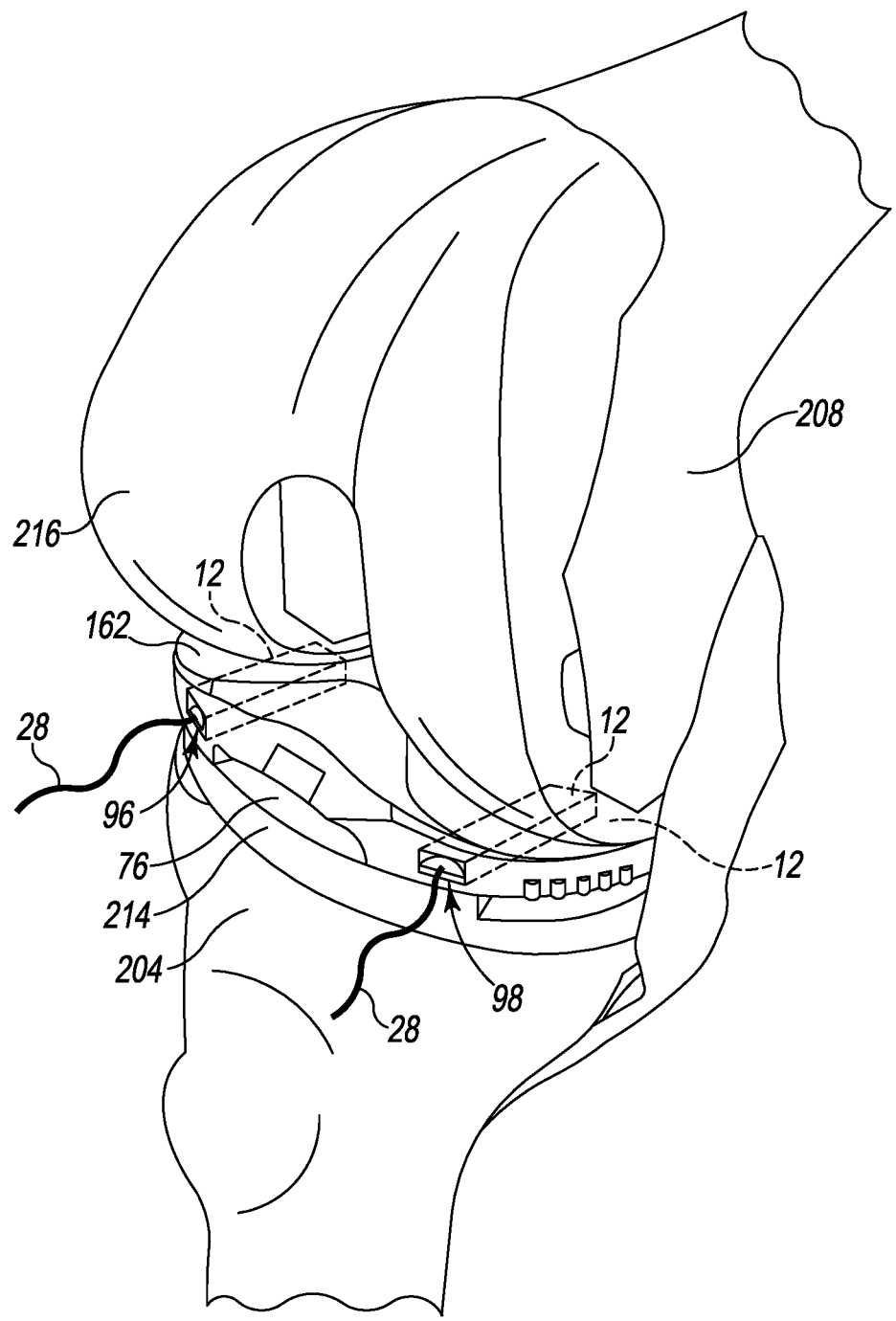

After trial reduction, the surgeon may select and insert final implant components. As shown in FIG. 18, the surgeon implants a final tibial tray component 214 into the patient's tibia 204 and a final femoral component 216 into the patient's femur 208. The surgeon selects a shim 76 (which may be the same shim 76 used during soft tissue balancing shown in FIG. 13 and/or trial reduction shown in FIG. 17), and attaches a pair of sensor adapters 12 (e.g., the sensor adapter 60) to the sensor connectors 34 included in the shim 76. The surgeon attaches the shim 76 to the insert trial 162, and then attaches the shim 76 to the final tibial component 214. As shown, after assembly, the articulation surface 166 of the insert trial 162 engages against the femoral component 216. During the surgical procedure, the femoral component 216 and the tibial tray component 214 exert forces on the insert trial 162 and the shim 76, respectively. Those forces are transferred to the sensor adapters 12, which generate force sensor data indicative of force and/or pressure across the entire knee joint. The surgeon may use the force sensor data to balance the knee joint, for example by balancing medial and lateral forces and/or by balancing anterior and posterior forces. The surgeon may move the knee joint between extension (shown in FIG. 18) and flexion to dynamically evaluate the forces in the joint throughout the range of motion. After assessing joint forces, the surgeon may remove the insert trial 162 (including the shim 76) and implant a final tibial insert.

Figure 19:
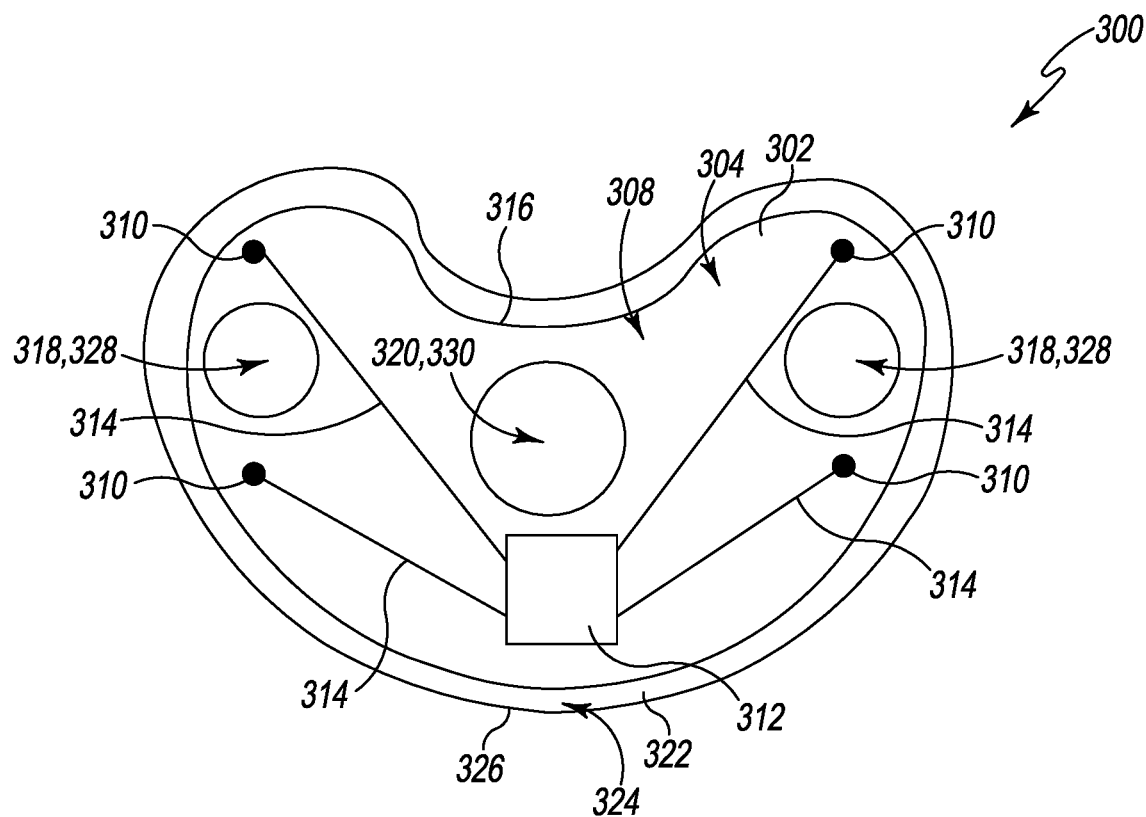
FIG. 19 is a plan view of a sensor system including a substrate and an alignment guide.
Figure 20:
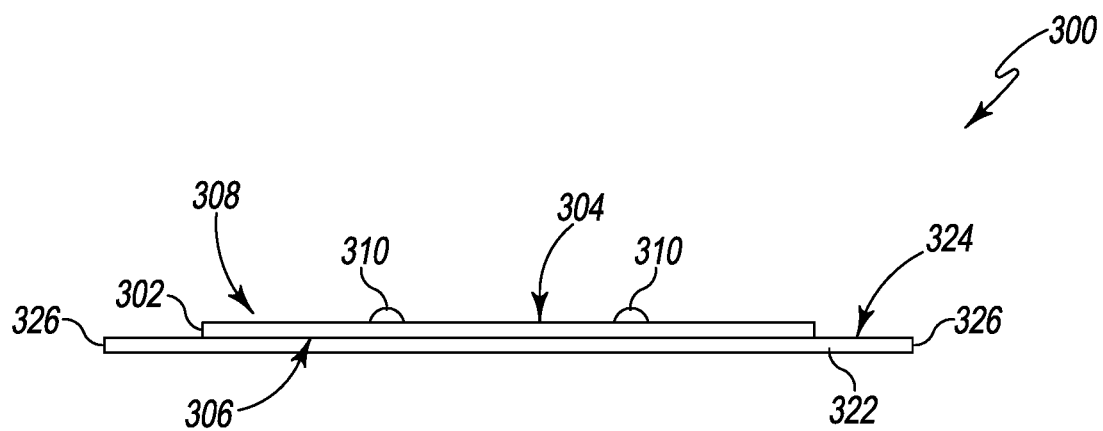
FIG. 20 is an elevation view of the sensor system of FIG. 19.

Referring now to FIGS. 19-20, a sensor system 300 for use in performing an orthopaedic surgical procedure includes a substrate 302 supporting one or more force sensors. The substrate 302 may be embodied as a plate, a circuit board, or any other suitable substrate capable of supporting force sensors and related electronics as described herein. In some embodiments, the substrate 302 may include one or more stiffening layers with known mechanical properties (e.g., stiffness). The substrate 302 includes a front side 304 and a back side 306, and the front side 304 includes an adhesive coating 308 for attachment to a surgical instrument. As described further below, the sensor system 300 may be attached to a surgical instrument such as a gap assessment tool, a balancer, a spacer block, a spacer base, a shim, a tibial trial component, and/or other surgical instruments used in a surgical procedure such as a total knee replacement procedure.

As shown, the sensor system 300 includes multiple sensor contacts 310 that extend outwardly from the front side 304 of the substrate 302. The sensor contacts 310 may be formed from an elastomeric material, a resilient polymeric material, a metallic material, or other material with known mechanical properties (e.g., stiffness). Each sensor contact 310 is configured to transfer force exerted on the sensor contact 310 to a force sensor 312 coupled to the substrate 302. The force sensor 312 may be embodied as any electronic force sensor, pressure sensor, or other sensor capable of measuring compression, such as a piezoelectric sensor, capacitive sensor, load cell, or other force sensor. The force sensor 312 may be attached to the front side 304, the back side 306, embedded in the substrate 302, or otherwise coupled to the substrate 302. The force sensor 312 is coupled to each sensor contact 310 via a corresponding trace 314 of the substrate 302. Additionally, although shown as including a single force sensor 312 coupled to multiple sensor contacts 310 via traces 314, it should be understood that the sensor system 300 may include a different number and/or arrangement of sensors 312 and/or traces 314. For example, in some embodiments, the sensor system 300 may include a sensor 312 coupled to each sensor contact 310 and/or each sensor contact 310 may include an integrated sensor 312.

Figure 31:
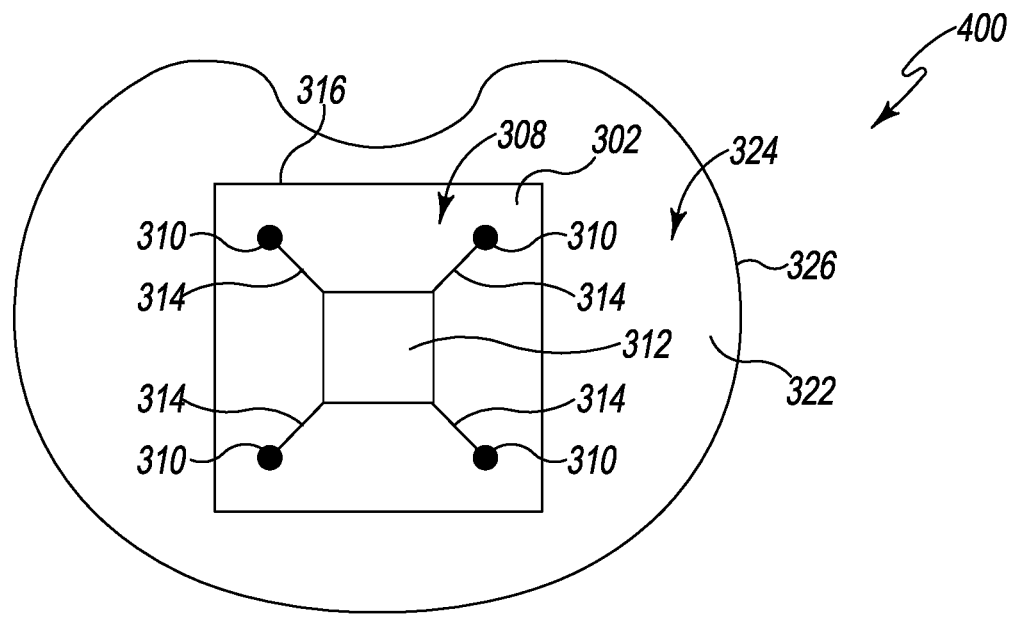
FIG. 31 is a plan view of another embodiment of a sensor system including a substrate and an alignment guide.
Figure 32:
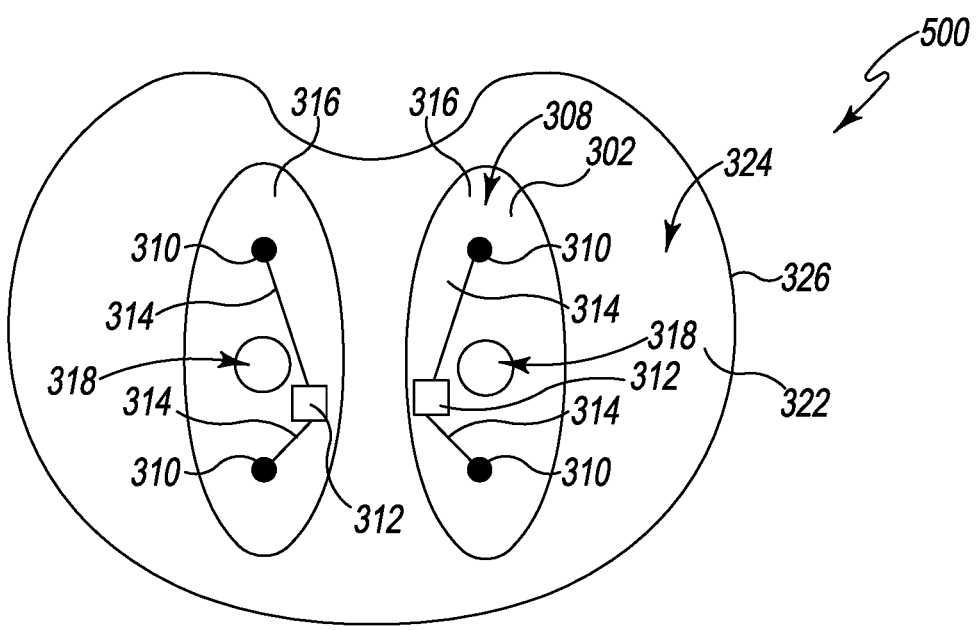
FIG. 32 is a plan view of another embodiment of a sensor system including multiple substrates and an alignment guide.

As shown in FIGS. 19-20, the illustrative substrate 302 has a kidney-shaped perimeter 316. As shown in FIGS. 21-30 and described further below, the perimeter 316 is shaped to fit within the footprint of one or more surgical instruments used with a total knee replacement procedure, such as a gap assessment tool, a balancer, a spacer block, a spacer base, a shim, and/or a tibial trial component. As such, the substrate 302 further includes a pair of lug holes 318 and a central hole 320 defined through the substrate 302. The holes 318, 320 may be configured to align with one or more features of a corresponding surgical instruments such as lugs, lug holes, passageways, or other features. Of course, in other embodiments, the substrate 302 may have a different shape. Examples of substrates 302 with different shapes and/or arrangements are illustrated in FIGS. 31-32 and described further below.

The substrate 302 may include one or more connectors, traces, wires, cables, or other components to connect the force sensor 312 to one or more external devices, such as a computer, a display, an external interface device, a transceiver, or other devices. The external device may be used to view, store, or otherwise process force data generated by the force sensor 312. Alternatively, in some embodiments, the substrate 302 may include a wireless communication circuit (e.g., one or more antenna loops or other wireless circuits) to communicate with external devices.

The sensor system 300 further includes an alignment guide 322 that is removably coupled to the back side 306 of the substrate 302. Illustratively, the alignment guide 322 includes an adhesive coating 324 for attachment to the substrate 302. The adhesive coatings 308, 324 may have different strengths such that the alignment guide 322 may be removed from the substrate 302 while the substrate 302 remains attached to a surgical instrument. Additionally or alternatively, the alignment guide 322 may be removably coupled to the substrate 302 using one or more clips, tabs, or other attachment mechanisms.

The illustrative alignment guide 322 has a kidney-shaped perimeter 326. As shown in FIGS. 21-30 and described further below, the perimeter 326 is shaped to match or otherwise align in a predetermined orientation relative to a surface of a surgical instrument used in a total knee replacement procedure, such as a gap assessment tool, a balancer, a spacer block, a spacer base, a shim, and/or a tibial trial component. The alignment guide 322 further includes a pair of lug holes 328 and a central hole 330 defined through the substrate. The holes 328, 330 are configured to receive and/or align with one or more features of the surgical instrument, such as lugs, posts, holes, passageways, or other features. As described further below, aligning the alignment guide 322 with the surgical instrument also aligns the substrate 302 (and thus the sensor contacts 310) in a predetermined location and orientation relative to the surgical instrument.

Although illustrated as including the perimeter 326 and the holes 328, 330, in other embodiments, the alignment guide 322 may include any combination of locating features that match or otherwise align the alignment guide 322 (and thus the attached substrate 302) in a predetermined location and orientation relative to a surgical instrument. For example, the alignment guide 322 may include one or more visual indicators (e.g., outlines, tick marks, or other indicators) that match corresponding features of the surgical instrument. As another example, the alignment guide 322 may include one or more slots, keys, openings, or other features that receive and/or are received by corresponding features of the surgical instrument. One potential embodiment of an alignment guide 322 that includes visual indicators is described below in connection with FIGS. 33-36.

Figure 21:
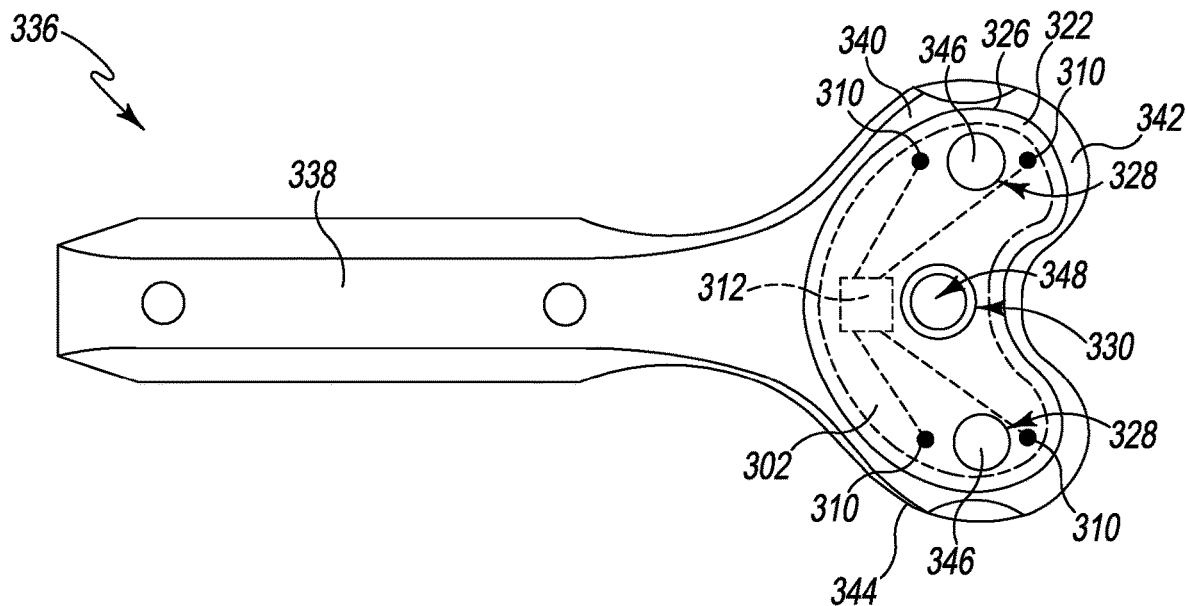
FIGS. 21-23 are views of the sensor system of FIGS. 19-20 attached to and for use with a gap assessment tool.
Figure 22:
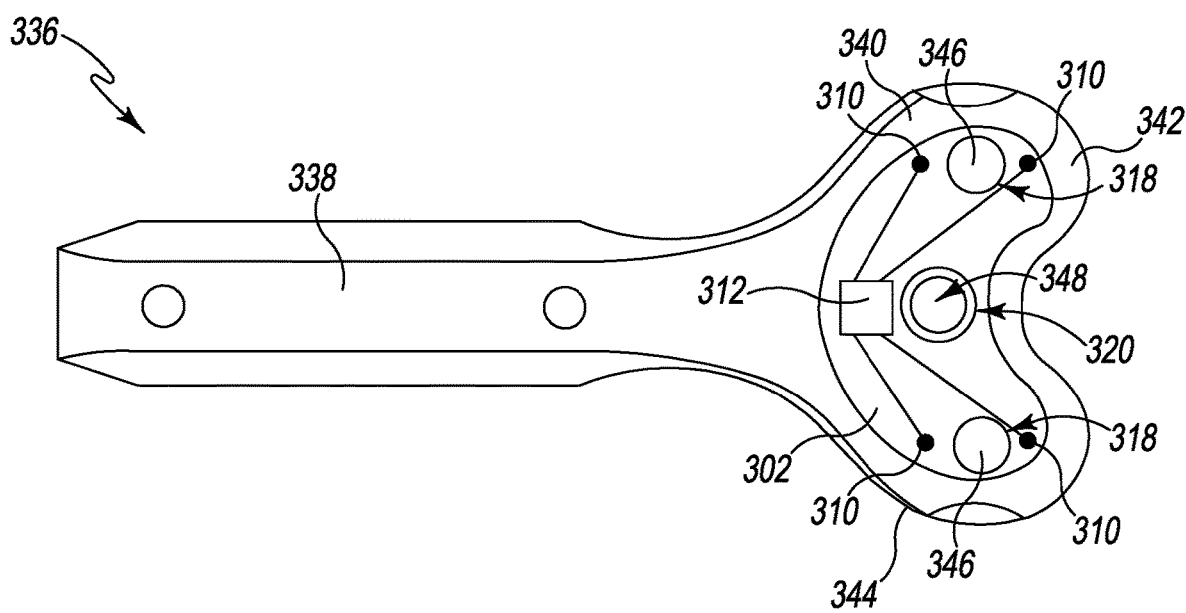
Figure 23:
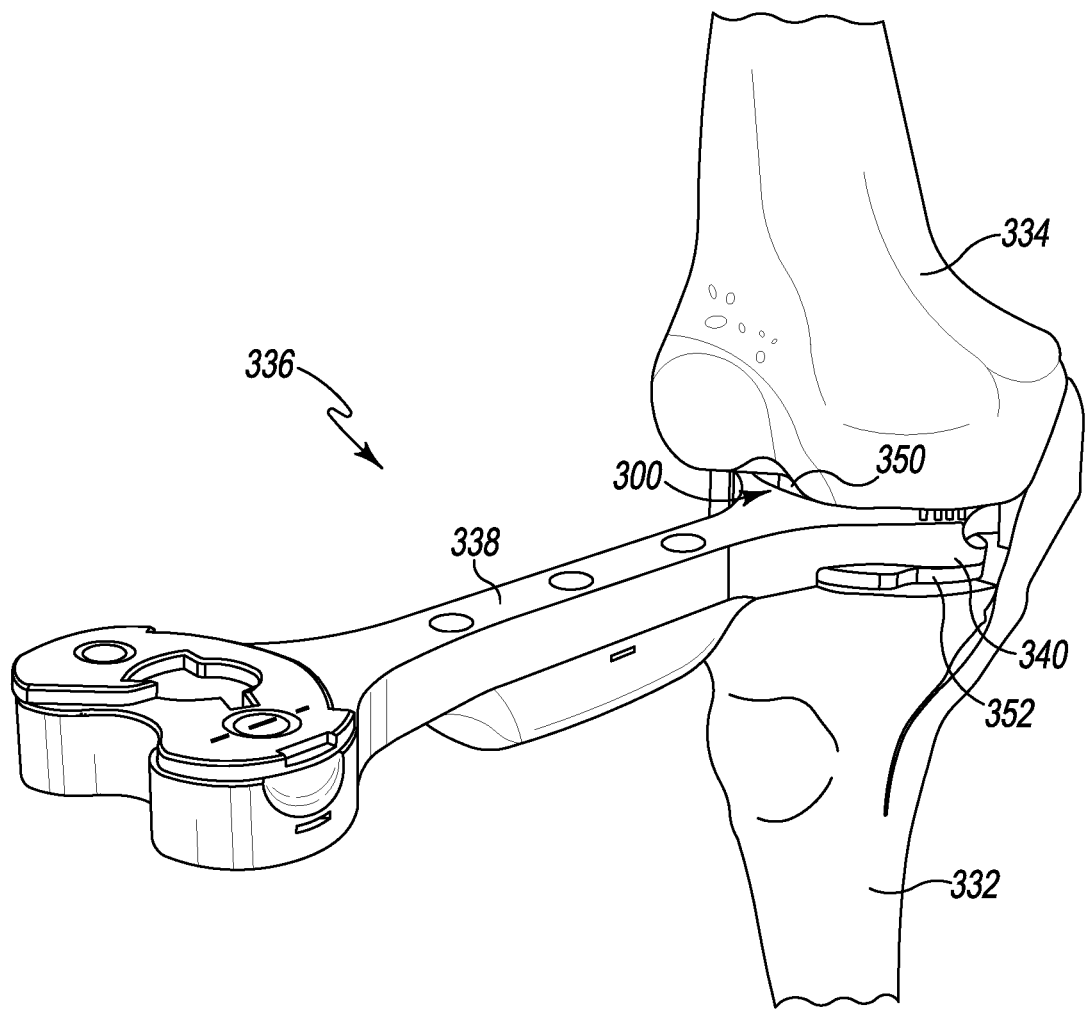

The sensor system 300 may be utilized during the performance of an orthopaedic surgical procedure similar to that shown in FIGS. 21-23. A surgeon initially prepares the knee joint, for example by resecting the proximal surface of a patient's tibia 332. After preparing the tibia 332, a gap is defined between the tibia and the patient's femur 334. The surgeon assess the flexion and extension gaps through the range of motion as described below.

A gap assessment tool 336 includes an elongated handle 338 as shown in FIGS. 21-22. The elongated handle 338 extends into a paddle-shaped spacer block 340. The spacer block 340 includes a proximal surface 342 and a distal surface opposite the proximal surface 342. The proximal surface 342 is surrounded by a perimeter 344. A pair of lugs 346 extend proximally from the proximal surface 342. A central bore 348 extends through the surfaces of the spacer block 340.

As shown in FIG. 21, the surgeon or other user may attach the sensor system 300 to the proximal surface 342 of the spacer block 340. The alignment guide 322 aligns the sensor system 300 with respect to the spacer block 340. Illustratively, the perimeter 326 of the alignment guide 322 fits within and/or otherwise matches the perimeter 344 of the proximal surface 342. Additionally, the lug holes 328 of the alignment guide 322 receive the lugs 346 of the spacer block 340, and the central hole 330 of the alignment guide 322 matches the central bore 348 of the spacer block 340.

The surgeon or other user presses the sensor system 300 against the proximal surface 342 such that the adhesive coating 308 of the substrate 302 attaches to the proximal surface 342. In some embodiments, the substrate 302 may be received in one or more recesses formed in the proximal surface 342 (not shown). As shown in FIG. 22, after attaching the substrate 302 to the proximal surface 342, the surgeon removes the alignment guide 322 from the substrate 302. The substrate 302 remains attached to the proximal surface 342.

After removing the alignment guide 322, the sensor contacts 310 are in contact with the proximal surface 342. Thus, compressive forces exerted on the spacer block 340 may be measured by the force sensor 312. As shown in FIG. 22, the sensor contacts 310 are distributed over the proximal surface 342 and thus may allow the force sensor 312 to measure forces experienced across multiple compartments of the patient's joint (e.g., medial/lateral, anterior/posterior, or otherwise across the joint).

After attaching the substrate 302 to the spacer block 340, the surgeon may complete assembly of the gap assessment tool 336, for example by attaching a shim 350 and/or a base 352 to the spacer block 340. With the patient's knee in extension as shown in FIG. 23, the surgeon inserts the assembled gap assessment tool 336 into the gap defined between the patient's tibia 332 and the femur 334. As shown, the shim 350 contacts the distal surface of the femur 334, and the base 352 contacts the resected surface of the tibia 332. With the gap assessment tool 336 inserted in the gap, the surgeon may distract the knee joint, for example by selecting a shim 350 of appropriate thickness, by extending one or more jacks to increase the thickness of the gap assessment tool 336, by using an external distractor (not shown), or using other techniques to apply tension to the knee joint.

During the surgical procedure, the femur 334 and the tibia 332 exert forces on the shim 350 and the base 352, respectively. Those forces are transferred via the sensor contacts 310 to the force sensor 312, which generates force sensor data indicative of force and/or pressure across the entire knee joint. The force sensor data may be communicated via wired and/or wireless communication to one or more external devices for display and/or storage.

When inserted in the joint, the sensor contacts 310 are located in predetermined positions relative to the joint. In particular, at least one sensor contact 310 may be positioned in each of the anterior-medial compartment, the posterior-medial compartment, the anterior-lateral compartment, and the posterior-lateral compartment of the knee joint.

The surgeon may use the force sensor data to balance the knee joint, for example by balancing medial and lateral forces and/or by balancing anterior and posterior forces. In some embodiments, for example when preparing a fixed bearing implant, the surgeon may use the force sensor data to assess rotational balance of the knee joint while rotating the gap assessment tool 336 about the nominal tibial internal-external rotation axis. The surgeon may rotate the gap assessment tool 336 until forces within the knee joint are sufficiently balanced. Further, the surgeon may move the knee between extension (shown in FIG. 23) and flexion to dynamically evaluate the forces in the joint throughout the range of motion.

Figure 24:
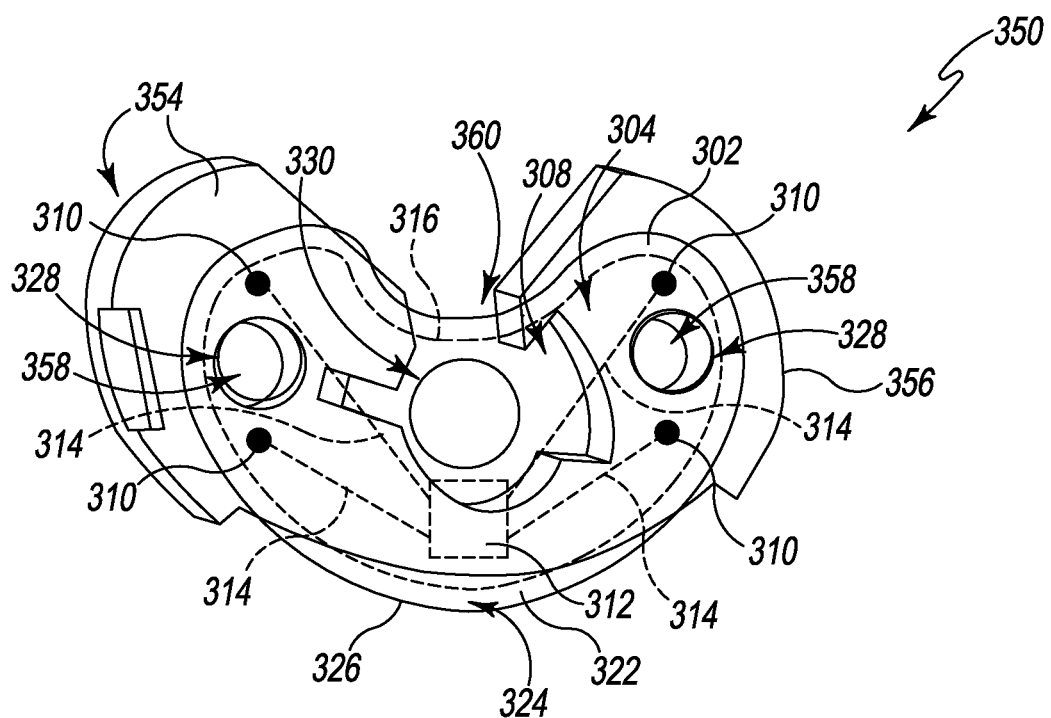
FIGS. 24-25 are views of the sensor system of FIGS. 19-20 attached to and for use with a shim.
Figure 25:
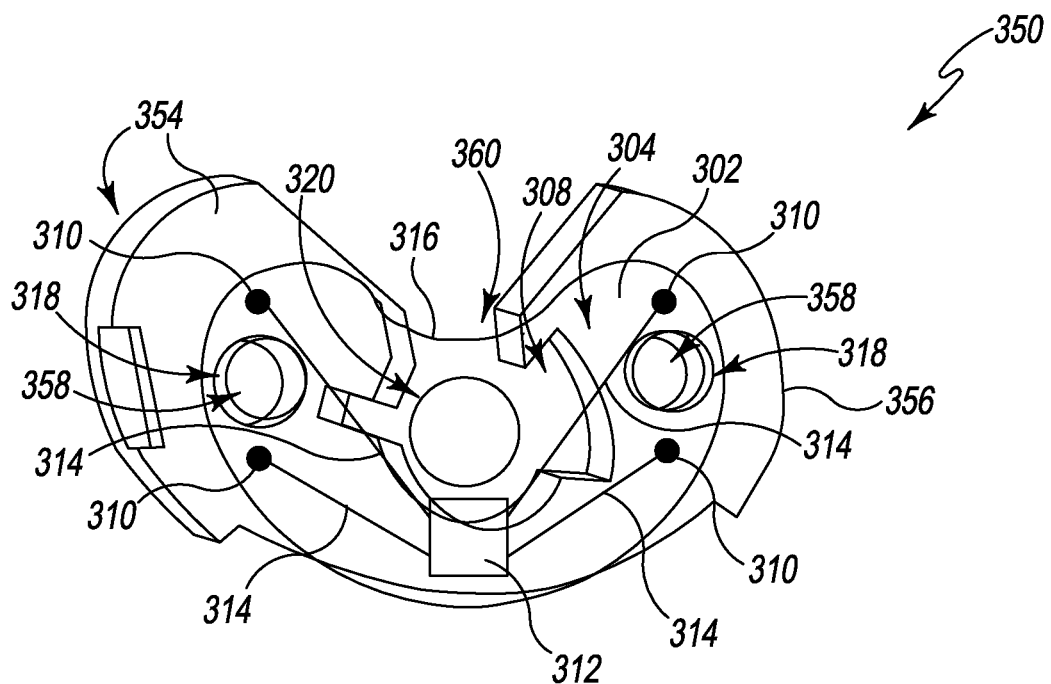

Referring now to FIGS. 24-25, in some embodiments the sensor system 300 may be utilized with a shim 350 during the performance of the surgical procedure, rather than the spacer block 340. The shim 350 includes a pair of opposing surfaces 354, which may be reversible. An outer wall 356 extends between the surfaces 354. The shim 350 has a predetermined thickness between the surfaces 354 (i.e., a height of the outer wall 50), such as five millimeters or six millimeters. In an embodiment, the gap assessment tool 336 may be used with multiple shims 350, each having a different thickness between the surfaces 354.

A pair of lug holes 358 extend through the surfaces 354. Each of the lug holes 358 is sized to receive a corresponding lug 346 of the spacer block 340. Each of the lugs 346 and/or lug holes 358 may include one or more retaining features such as spring retainers to retain the shim 350 against the spacer block 340. A central opening 360 is further defined in the shim 350.

As shown in FIG. 24, the surgeon or other user may attach the sensor system 300 to a surface 354 of the shim 350. The alignment guide 322 aligns the sensor system 300 with respect to the shim 350. Illustratively, the perimeter 326 of the alignment guide 322 fits within and/or otherwise matches the outer wall 356 of the shim 350. Additionally, the lug holes 328 of the alignment guide 322 align with the lug holes 358 of the shim 350, and the central hole 330 of the alignment guide 322 matches the central opening 360 of the shim 350.

The surgeon or other user presses the sensor system 300 against the surface 354 such that the adhesive coating 308 of the substrate 302 attaches to the surface 354. In some embodiments, the substrate 302 may be received in one or more recesses formed in the surface 354 (not shown). As shown in FIG. 25, after attaching the substrate 302 to the surface 354, the surgeon removes the alignment guide 322 from the substrate 302. The substrate 302 remains attached to the surface 354.

After removing the alignment guide 322, the sensor contacts 310 are in contact with the surface 354. Thus, compressive forces exerted on the shim 350 may be measured by the force sensor 312. As shown in FIG. 25, the sensor contacts 310 are distributed over the surface 354 and thus may allow the force sensor 312 to measure forces experienced across multiple compartments of the patient's joint (e.g., medial/lateral, anterior/posterior, or otherwise across the joint).

After attaching the substrate 302 to the shim 350, the surgeon may complete assembly of the gap assessment tool 336, for example by attaching the shim 350 to the spacer block 340 and then attaching a base 352 to the spacer block 340. The surgeon may proceed with balancing the patient's knee using the assembled gap assessment tool 336 including the attached force sensor 312 as shown in FIG. 23 and described above.

Figure 26:
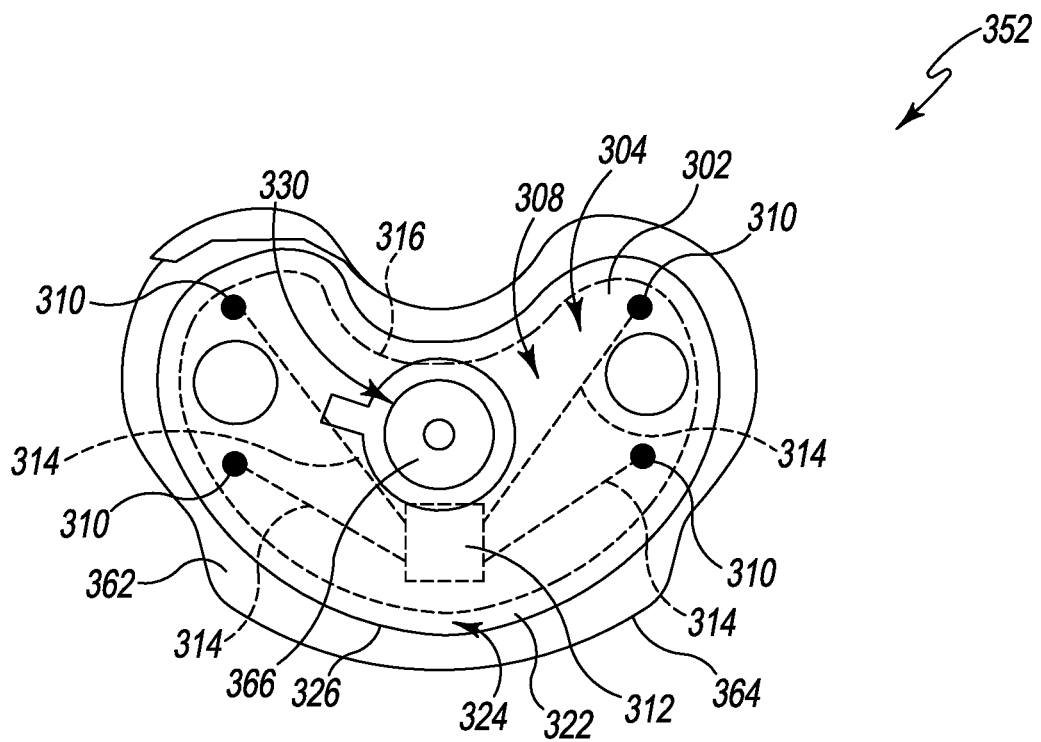
FIGS. 26-27 are views of the sensor system of FIGS. 19-20 attached to and for use with a spacer base.
Figure 27:
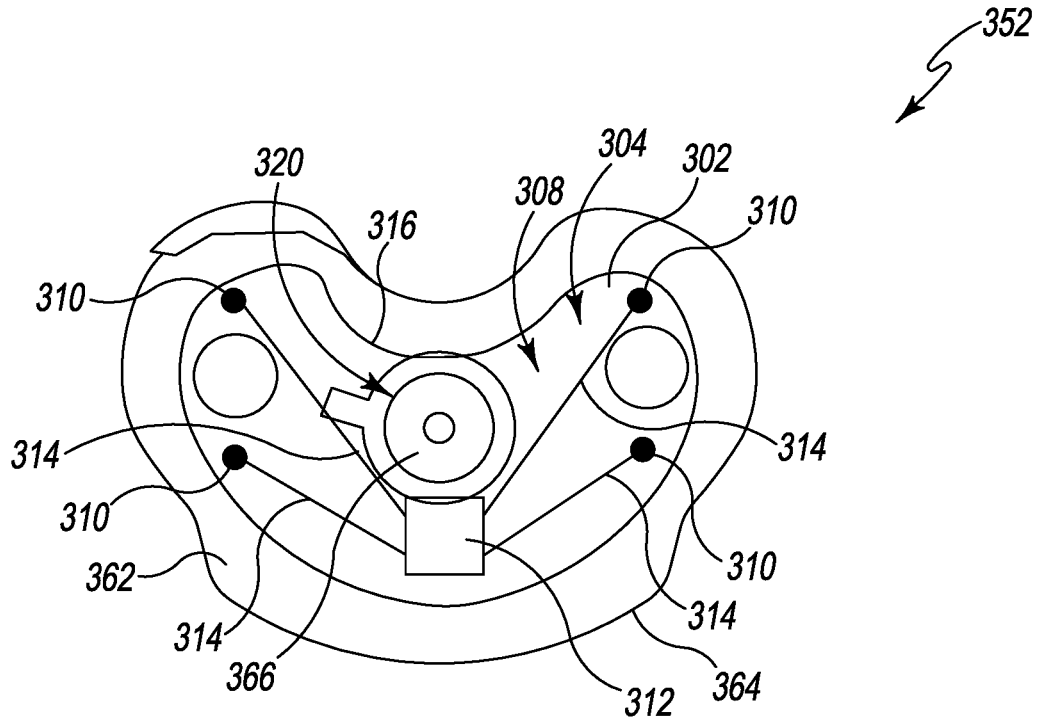

Referring now to FIGS. 26-27, in some embodiments the sensor system 300 may be utilized with a base 352 during the performance of the surgical procedure, rather than the spacer block 340 or the shim 350. The base 352 includes a proximal surface 372 and a distal surface opposite the proximal surface 372. An outer wall 364 extends between those surfaces. As described further below, the proximal surface 372 is shaped to match and receive the spacer block 340. In some embodiments, the proximal surface 372 may further include keys or other features that match the spacer block 340 in a particular predetermined orientation. The distal surface may include a tibial conforming surface for contacting a patient's surgically prepared tibia 332. The base 352 further includes a central stud 366 that extends outwardly from the proximal surface 372. The stud 366 fits within the central bore 348 of the spacer block 340. The stud 366 may include a hog ring or other feature to retain the base 352 against the spacer block 340.

As shown in FIG. 26, the surgeon or other user may attach the sensor system 300 to the proximal surface 372 of the base 352. The alignment guide 322 aligns the sensor system 300 with respect to the base 352. Illustratively, the perimeter 326 of the alignment guide 322 fits within and/or otherwise matches the outer wall 364 surrounding the proximal surface 372. Additionally, the central hole 330 of the alignment guide 322 receives the stud 366 of the base 352.

The surgeon or other user presses the sensor system 300 against the proximal surface 372 such that the adhesive coating 308 of the substrate 302 attaches to the proximal surface 372. In some embodiments, the substrate 302 may be received in one or more recesses formed in the proximal surface 372 (not shown). As shown in FIG. 27, after attaching the substrate 302 to the proximal surface 372, the surgeon removes the alignment guide 322 from the substrate 302. The substrate 302 remains attached to the proximal surface 372.

After removing the alignment guide 322, the sensor contacts 310 are in contact with the proximal surface 372. Thus, compressive forces exerted on the base 352 may be measured by the force sensor 312. As shown in FIG. 27, the sensor contacts 310 are distributed over the proximal surface 372 and thus may allow the force sensor 312 to measure forces experienced across multiple compartments of the patient's joint (e.g., medial/lateral, anterior/posterior, or otherwise across the joint).

After attaching the substrate 302 to the base 352, the surgeon may complete assembly of the gap assessment tool 336, for example by attaching a shim 350 to the spacer block 340 and then attaching the base 352 to the spacer block 340. The surgeon may proceed with balancing the patient's knee using the assembled gap assessment tool 336 including the attached force sensor 312 as shown in FIG. 23 and described above.

Figure 28:
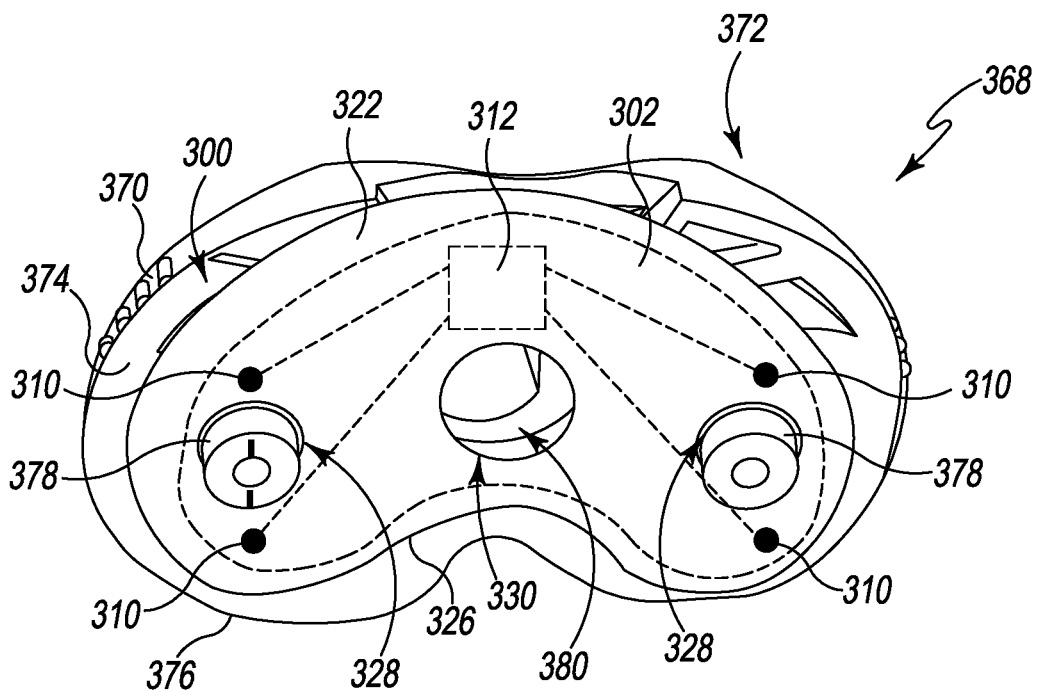
FIGS. 28-30 are views of the sensor system of FIGS. 19-20 attached to and for use with a tibial trial component.
Figure 29:
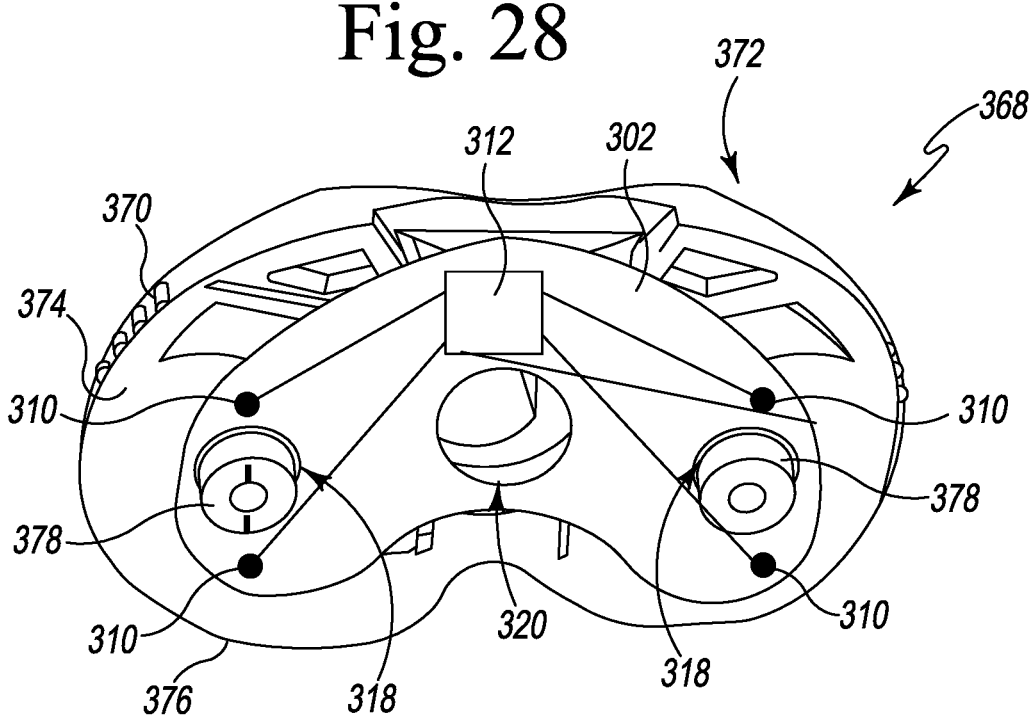
Figure 30:
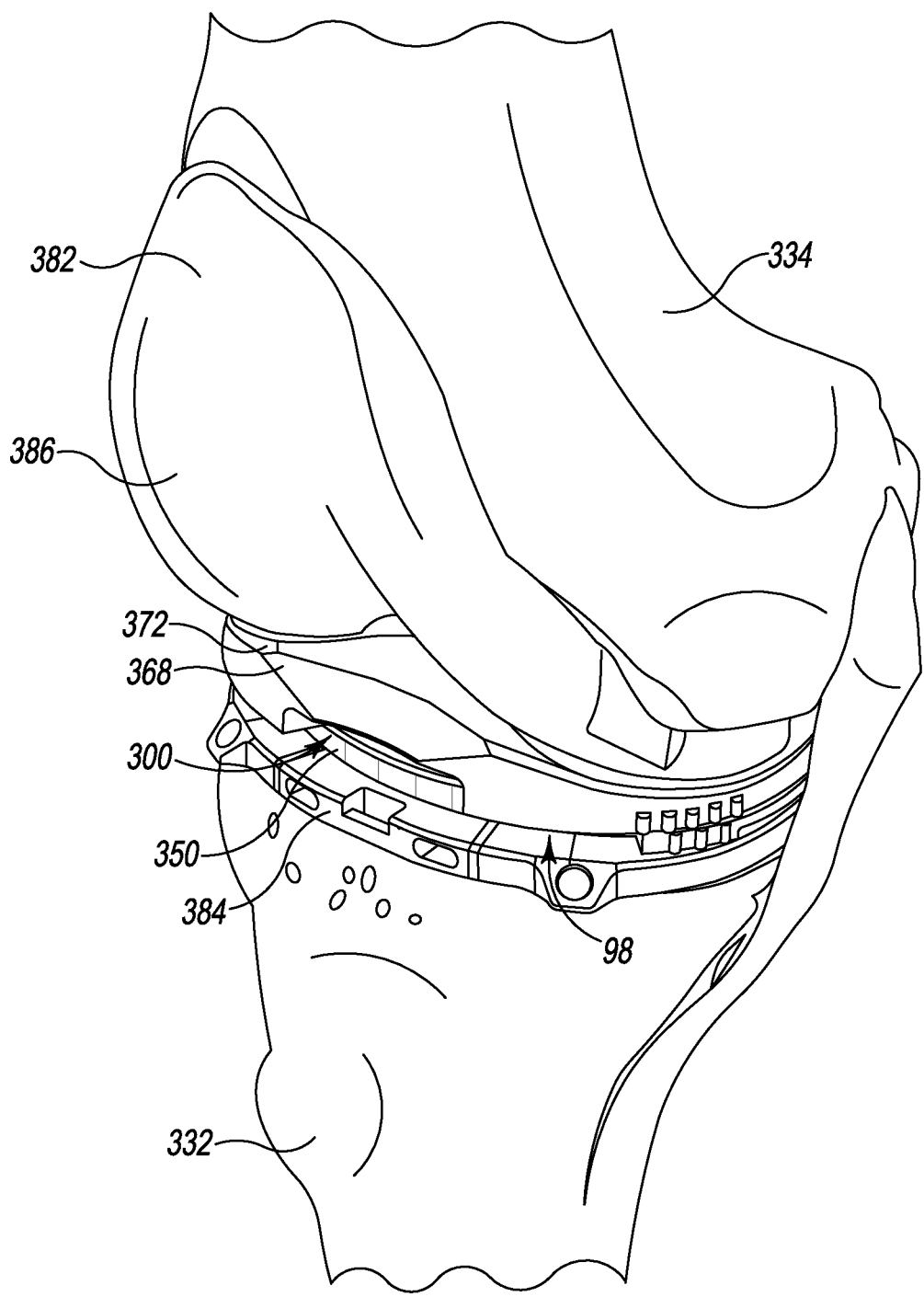

The sensor system 300 may also be utilized during the performance of an orthopaedic surgical procedure similar to that shown in FIGS. 28-30. A surgeon initially prepares the knee joint, for example by resecting the proximal surface of the patient's tibia 332, resecting the distal surface of the femur 334, and reaming the medullary canal of the tibia 332 and the femur 334. After preparing the femur 334, the surgeon next performs a trial reduction of the patient's knee joint as described below.

A tibial insert trial 368, also called an articulation surface trial 368, includes body 370 which is illustratively formed from a resilient plastic material. The insert trial 368 includes an upper, articulation surface 372 and a lower, distal surface 374. An outer perimeter wall 376 extends between the surfaces 372, 374 and surrounds the insert trial 368. As described further below, the articulation surface 372 is profiled to match and receive a femoral trial component, and the distal surface 374 is shaped to match and receive a shim 350. In particular, a pair of lugs 378 extend outwardly from the distal surface 374. Similar to the lugs 346 of the gap assessment tool 336, the lugs 378 may be received by corresponding lug holes 358 of the shim 350. The distal surface 374 further includes a central passageway 380 extending upward into the insert trial 368. In some embodiments, the distal surface 374 may also include keys or other features that match the shim 350 and/or another component such as a tibial base trial in a particular predetermined orientation.

As shown in FIG. 28, the surgeon or other user may attach the sensor system 300 to the distal surface 374 of the insert trial 368. The alignment guide 322 aligns the sensor system 300 with respect to the insert trial 368. Illustratively, the perimeter 326 of the alignment guide 322 fits within and/or otherwise matches the perimeter wall 376 surrounding the distal surface 374. Additionally, the lug holes 328 of the alignment guide 322 receive the lugs 378 of the insert trial 368, and the central hole 330 of the alignment guide 322 matches the central passageway 380 of the insert trial 368.

The surgeon or other user presses the sensor system 300 against the distal surface 374 such that the adhesive coating 308 of the substrate 302 attaches to the distal surface 374. In some embodiments, the substrate 302 may be received in one or more recesses formed in the distal surface 374 (not shown). As shown in FIG. 29, after attaching the substrate 302 to the distal surface 374, the surgeon removes the alignment guide 322 from the substrate 302. The substrate 302 remains attached to the distal surface 374.

After removing the alignment guide 322, the sensor contacts 310 are in contact with the distal surface 374. Thus, compressive forces exerted on the insert trial 368 may be measured by the force sensor 312. As shown in FIG. 29, the sensor contacts 310 are distributed over the distal surface 374 and thus may allow the force sensor 312 to measure forces experienced across multiple compartments of the patient's joint (e.g., medial/lateral, anterior/posterior, or otherwise across the joint).

After attaching the substrate 302 to the insert trial 368, the surgeon proceeds with trial reduction. The surgeon inserts a femoral trial component 382 into the surgically prepared femur 334. After preparing the tibia 332, the surgeon inserts a tibial base trial 384 into the surgically prepared tibia 332. The surgeon assembles a tibial trial stack by selecting a shim 350 and attaching the selected shim 350 to the insert trial 368, and then attaching the shim 350 to the tibial base trial 384. As shown in FIG. 30, after assembly, the articulation surface 372 of the insert trial 368 engages against a bearing surface 386 of the femoral trial component 382. The surgeon may distract the knee joint, for example by selecting a shim 350 of appropriate thickness, by extending one or more jacks to increase the thickness of the tibial trial stack, by using an external distractor (not shown), or using other techniques to apply tension to the knee joint.

During the surgical procedure, the tibia 332 and the femur 334 (and/or the corresponding tibial base trial 384 and femoral trial component 374) exert forces on the shim 350 and the insert trial 368, respectively. Those forces are transferred via the sensor contacts 310 to the force sensor 312, which generates force sensor data indicative of force and/or pressure across the entire knee joint. The force sensor data may be communicated with wired and/or wireless communication to one or more external devices for display and/or storage.

The surgeon may use the force sensor data to balance the knee joint, for example by balancing medial and lateral forces and/or by balancing anterior and posterior forces. The surgeon may move the knee joint between extension (shown in FIG. 30) and flexion to dynamically evaluate the forces in the joint throughout the range of motion.

Although illustrated in FIGS. 28-30 as using the sensor system 300 attached to the insert trial 368, it should be understood that in some embodiments a similar procedure may be performed by attaching the sensor system 300 to the shim 350 as shown in FIGS. 24-25 and then performing trial reduction using the shim 350 with attached substrate 302.

Referring now to FIG. 31, another embodiment of a sensor system 400 includes a substrate 302 having a rectangular perimeter 316. Similar to the sensor system 300 shown in FIGS. 19-30, the sensor system 400 may be attached to a surgical instrument using the alignment guide 322. The substrate 302 may be received in a recess matching the rectangular perimeter 316 (e.g., a rectangular recess).

Similarly, and referring now to FIG. 32, another embodiment of a sensor system 500 includes a pair of substrates 302 each having an oval-shaped perimeter 316. Each substrate 302 includes independent sensor contacts 310 and force sensors 312. Similar to the sensor system 300, 400 shown in FIGS. 19-31, the sensor system 500 may be attached to a surgical instrument using the alignment guide 322. Each substrate 302 may be received in a corresponding recess matching the perimeter 316 (e.g., a pair of oval-shaped recesses).

Figure 33:
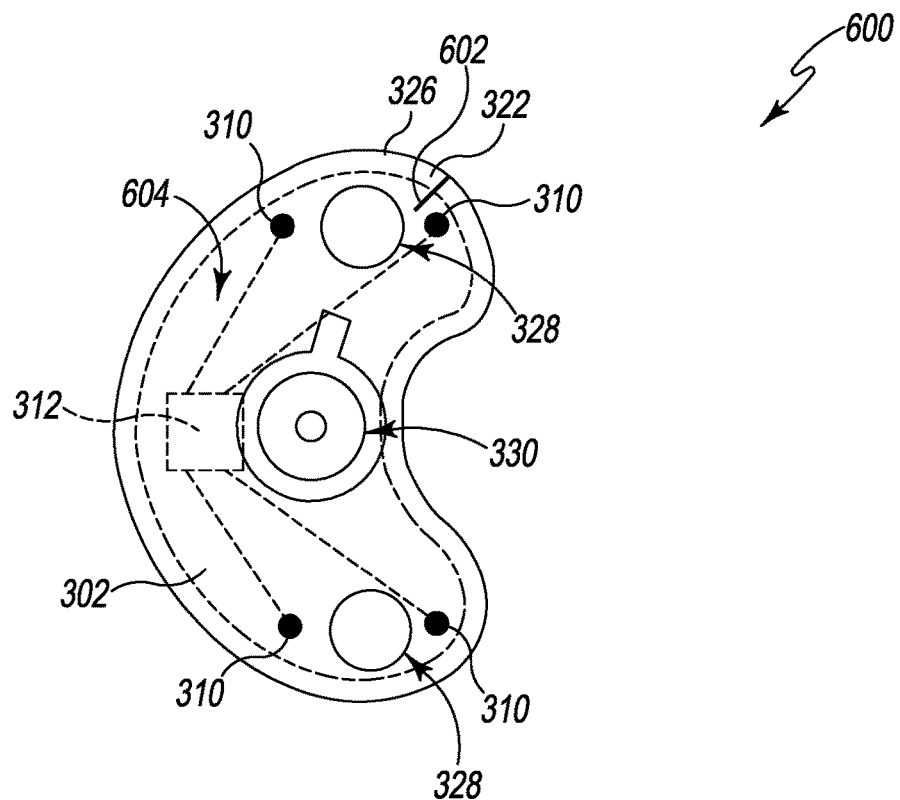
FIG. 33 is a plan view of a sensor system including a substrate and an alignment guide including a visual indicator.

Referring now to FIG. 33, in another embodiment, a sensor system 600 for use in performing an orthopaedic surgical procedure includes a substrate 302 that is removably coupled to an alignment guide 322. The substrate 302 and the alignment guide 322 are similar to the substrate 302 and the alignment guide 322 illustrated in FIGS. 19-20, the description of which is also applicable to the sensor system 600, and which is not repeated herein. Additionally, as shown in FIG. 33, the substrate 322 of the sensor system 600 includes a tick mark 602, which, as described further below, is a visible indicator that matches one or more features of a corresponding surgical instrument. The tick mark 602 is printed, engraved, or otherwise positioned on a back side 604 of the alignment guide 322. The back side 604 is positioned opposite the substrate 302 and thus is visible to a user when applying the substrate 302 to a surgical instrument. Although illustrated as including a single tick mark 602, in other embodiments the alignment guide 322 may include any number and/or type of visual indicators, such as outlines, tick marks, lettering, markings, or other indicators.

Figure 34:
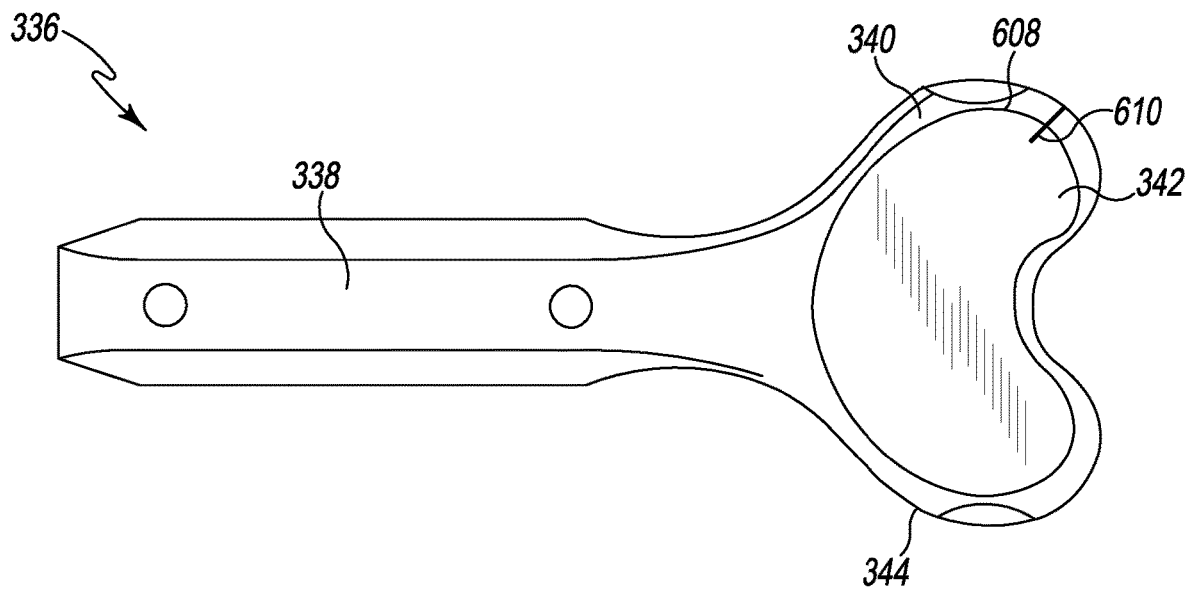
FIG. 34 is a plan view of a gap assessment tool for use with the sensor system of FIG. 33.
Figure 35:
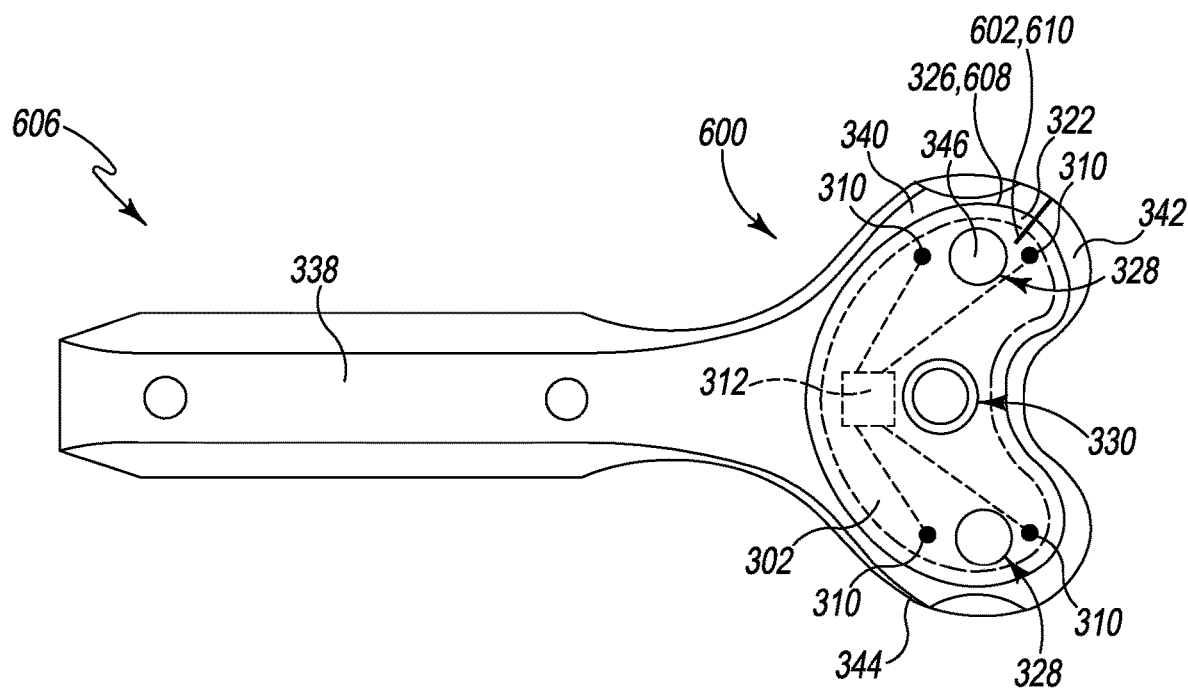
FIGS. 35-36 are views of the sensor system of FIG. 33 attached to and for use with the gap assessment tool of FIG. 34.
Figure 36:
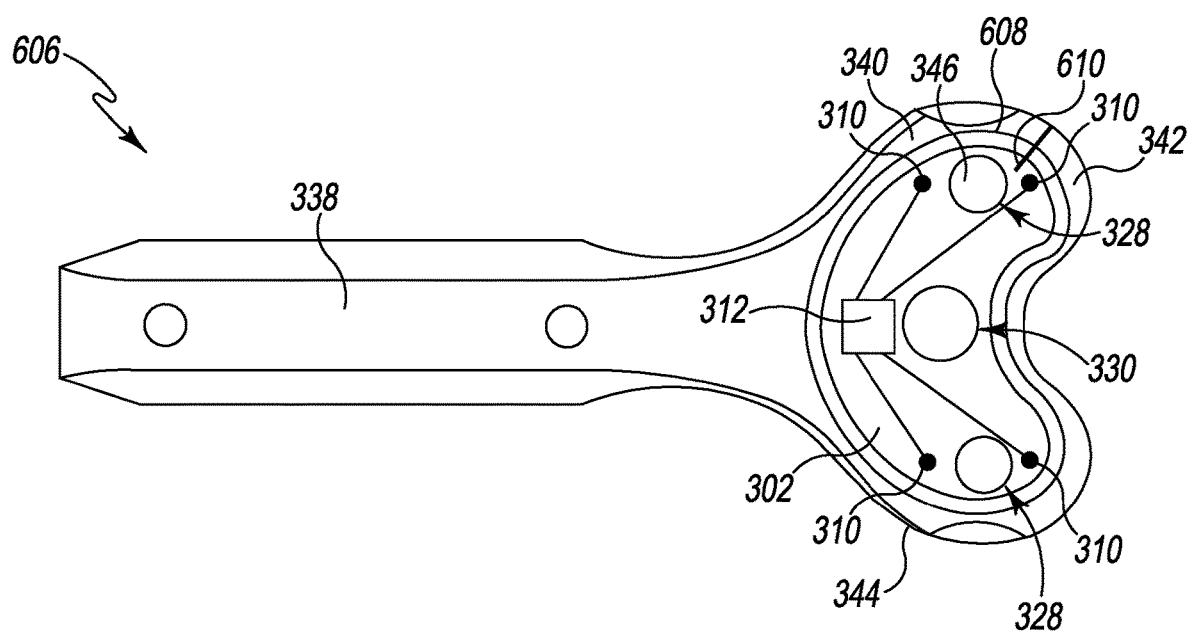

The sensor system 600 may be utilized during the performance of an orthopaedic surgical procedure similar to that shown in FIGS. 34-36. A surgeon initially prepares the knee joint, for example by resecting the proximal surface of a patient's tibia. After preparing the tibia, a gap is defined between the tibia and the patient's femur. The surgeon assess the flexion and extension gaps through the range of motion as described below.

A gap assessment tool 606 includes an elongated handle 338 as shown in FIGS. 34-36. The elongated handle 338 extends into a paddle-shaped spacer block 340. The spacer block 340 includes a proximal surface 342 and a distal surface opposite the proximal surface 342. The proximal surface 342 is surrounded by a perimeter 344. The illustrative proximal surface 342 of the gap assessment tool 606 is substantially flat and does not include lugs or a central bore. As shown in FIG. 34, an outline 608 and a tick mark 610 are printed, engraved, or otherwise positioned on the proximal surface 342 of the spacer block 340.

As shown in FIG. 35, the surgeon or other user may attach the sensor system 600 to the proximal surface 342 of the spacer block 340. The alignment guide 322 aligns the sensor system 600 with respect to the spacer block 340. Illustratively, the tick mark 602 displayed on the alignment guide 322 aligns with the tick mark 610 displayed on the proximal surface 342 of the spacer block 340. Additionally, the perimeter 326 of the alignment guide 322 aligns with the outline 608 displayed on the proximal surface 342. Note that the lug holes 328 and/or the central hole 330 of the alignment guide 322 may not align with any particular features of the spacer block 340.

The surgeon or other user presses the sensor system 300 against the proximal surface 342 such that the adhesive coating 308 of the substrate 302 attaches to the proximal surface 342. As shown in FIG. 36, after attaching the substrate 302 to the proximal surface 342, the surgeon removes the alignment guide 322 from the substrate 302. The substrate 302 remains attached to the proximal surface 342.

After removing the alignment guide 322, the sensor contacts 310 are in contact with the proximal surface 342. Thus, compressive forces exerted on the spacer block 340 may be measured by the force sensor 312. As shown in FIG. 36, the sensor contacts 310 are distributed over the proximal surface 342 and thus may allow the force sensor 312 to measure forces experienced across multiple compartments of the patient's joint (e.g., medial/lateral, anterior/posterior, or otherwise across the joint).

After attaching the substrate 302 to the spacer block 340, the surgeon may complete assembly of the gap assessment tool 606, for example by attaching a shim 350 and/or a base 352 to the spacer block 340. After completing assembly of the gap assessment tool 606, the surgeon may then proceed to balance the patient's knee joint using force sensor data as described above.

Additionally or alternatively, in some embodiments a sensor system may be attached between surgical instruments and/or between parts of a surgical instrument. For example, in an embodiment a surgical instrument may include multiple instruments, sub-instruments, or other parts in a clamshell configuration (i.e., connected with a hinge or other rotatable connection). In that embodiment, a sensor system may be attached to a surface of one part of the surgical instrument, the alignment guide may be removed from the substrate, and then another part of the surgical instrument may be rotated to close the surgical instrument and cover the substrate. In those embodiments, the substrate and other components of the sensor system may be contained by the surgical instrument and thus may not be required to be sterile.

Figure 37:
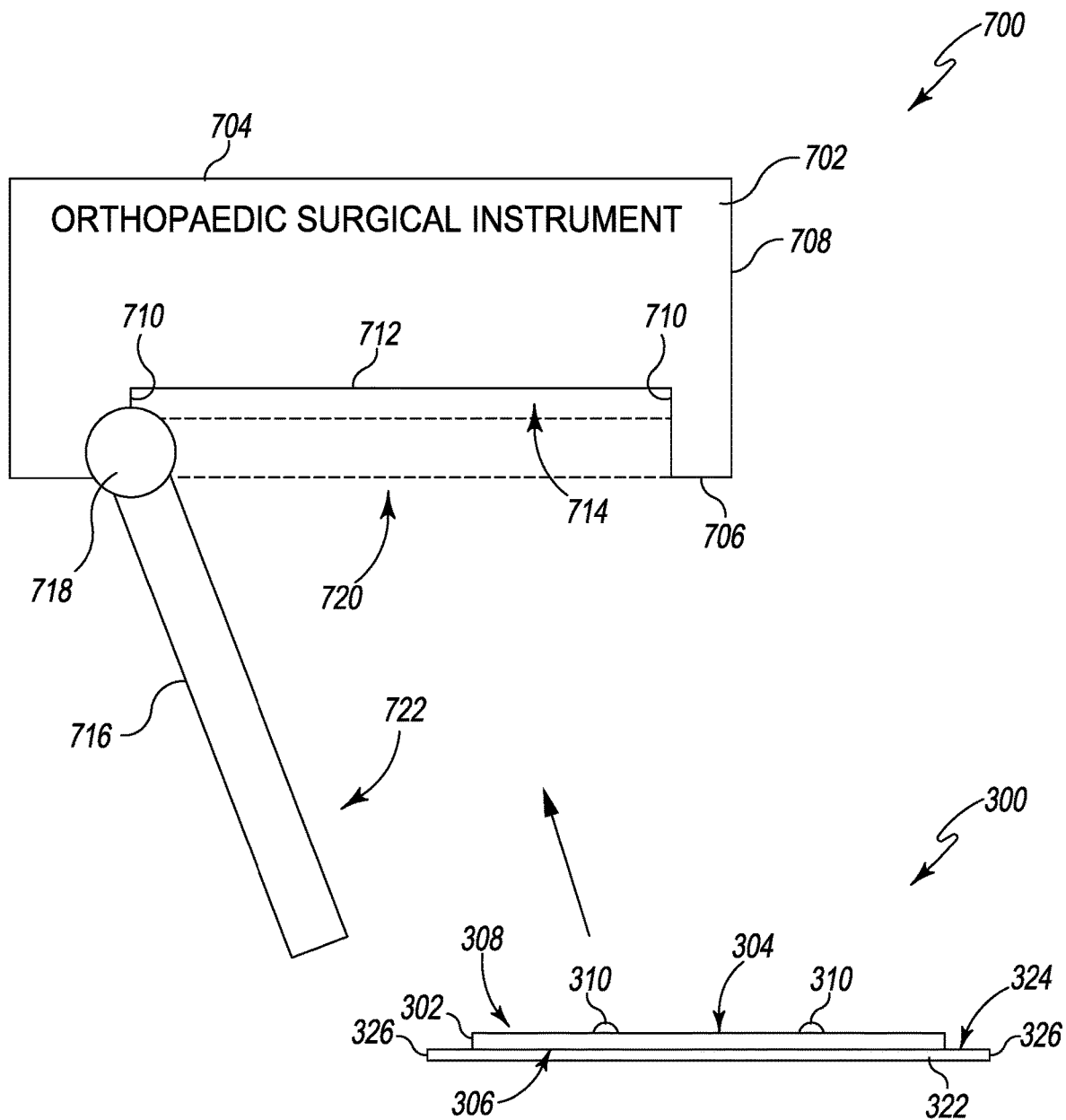
FIG. 37 is a schematic view of a sensor system and a surgical instrument including a sensor compartment.

Referring now to FIG. 37, in some embodiments, an orthopaedic surgical instrument 700 may include an inner chamber with a movable cover for receiving a sensor system 300. Similar to the surgical instruments 32 described above, the instrument 700 may be embodied as a surgical saw, a gap assessment tool, a spacer block, a shim, a balancer, a lamina spreader, a femoral sizer, a trial component, a tensioner, and/or another surgical instrument used in a surgical procedure such as a total knee replacement procedure.

The surgical instrument 700 includes a body 702, which may be formed from a resilient polymeric material, a metallic material, or other suitable material. The body 702 includes an upper surface 704, a lower surface 706, and an outer wall 708 extending between the surfaces 704, 706. Each of the surfaces 704, 706 may be flat, curved, or otherwise shaped. Additionally, it should be understood that the terms "upper" and "lower" with regard to the surfaces 704, 706 are for illustrative purposes only, and that the surgical instrument 700 may be used in any appropriate orientation relative to a patient's anatomy.

Illustratively, one or more inner walls 710 extend inwardly from the lower surface 706 toward an end wall 712. The inner walls 710 and the end wall 712 define a sensor compartment 714 within the surgical instrument 700. The surgical instrument 700 further includes a moveable cover 716 coupled to the body 702 with a hinge 718. When moved to a closed position 720, the cover 716 covers the sensor compartment 714, and when moved to an open position 722, the cover 716 reveals the sensor compartment 714. In some embodiments, the sensor compartment 700 may include one or more springs, latches, detents, or other devices to bias or otherwise secure the cover 716 in the closed position 720 and/or in the open position 722. Additionally or alternatively, although illustrated as being connected to the body 702 by the hinge 718, in other embodiments the cover 716 may be moveably coupled to the body 702 using any mechanical joint or other appropriate technique. Further, although illustrated as being defined in the lower surface 706, it should be understood that the sensor compartment 714 may be defined on any appropriate side of the surgical instrument 700.

In use, a surgeon or other user may move the cover 716 from the closed position 720 to the open position 722 to reveal the sensor compartment 714. When in the open position 722, the sensor compartment 714 is accessible from outside the surgical instrument 700. The sensor compartment 714 is configured to receive the substrate 302 and/or the substrate 302 and the alignment guide 322 of the sensor system 300. Upon moving the cover 716 to the open position 722, the user may attach the sensor system 300 to the end wall 712 within the sensor compartment 714. The alignment guide 322 may align the sensor system 300 with respect to the surgical instrument 700, for example by fitting within and/or otherwise matching the inner walls 710 that define the sensor compartment 714. As another example, the alignment guide 322 may align with or otherwise match one or more external features of the surgical instrument 700, such as an external perimeter of the surgical instrument 700, one or more lugs or other features extending from the surgical instrument 700, one or more visual indicators positioned on the surgical instrument 700, one or more openings defined in the surgical instrument 700, or other features of the surgical instrument 700.

The surgeon or other user presses the sensor system 300 against the end wall 712 such that the adhesive coating 308 of the substrate 302 attaches to the end wall 712. After attaching the substrate 302 to the end wall 712, the surgeon removes the alignment guide 322 from the substrate 302. The substrate 302 remains attached to the end wall 712 and thus remains positioned within the sensor compartment 714. The surgeon moves the cover 716 from the open position 722 to the closed position 720, covering both the sensor compartment 714 and the substrate 302.

After removing the alignment guide 322, the sensor contacts 310 are in contact with the end wall 712. Thus, compressive forces exerted on the surgical instrument 700 may be measured by the force sensor 312. In particular, compressive forces experienced by the surfaces 704, 706 of the instrument 700 may be transferred to the force sensor 312 via the sensor contacts 310 and the end wall 712. The body 702 of the instrument 700 and/or the cover 716 may flex or otherwise deflect a small amount (for example, a few tenths of a millimeter) in order to allow compressive forces to transfer to the sensor adapter 312. In some embodiments, the instrument 700 may include a hinge, a relief, or other flexible component to allow such deflection. In some embodiments, multiple parts of the body 702 and/or the cover 716 may deflect independently such that force may be transferred separately to each of the sensor contacts 310.

Although illustrated as being used in a total knee replacement, it should be understood that the concepts disclosed herein may be used in other surgical procedures. For example, the concepts disclosed herein may be used in a shoulder replacement surgery, a hip replacement surgery, or other joint replacement or revision surgery.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical instrument system for an orthopaedic surgical procedure, the system comprising:
 a sensor adapter including:
  a housing having a first surface;
  a force sensor positioned within the housing; and
  a sensor contact extending from the first surface of the housing, wherein the sensor contact is configured to transfer force exerted on the sensor contact to the force sensor; and
 a plurality of surgical instruments, wherein each of the plurality of surgical instruments includes:
  a sensor connector configured to receive the sensor adapter at a predetermined location relative to the surgical instrument, the sensor connector comprising an inner wall extending inwardly from an outer wall of the surgical instrument to define a passageway in the outer wall that is sized to receive the housing of the sensor adaptor; and
  a registering feature configured to engage an anatomical feature of a patient or another surgical instrument of the plurality of surgical instruments, wherein the registering feature has a predetermined location relative to the sensor connector;
 wherein, when the housing of the sensor adaptor is received in the passageway of a first surgical instrument of the plurality of surgical instruments, (i) the inner wall of the first surgical instrument is configured to confront the first surface of the sensor adaptor and (ii) the inner wall of the first surgical instrument is configured to engage the sensor contact.

2. The system of claim 1, wherein when the sensor adapter is coupled to the sensor connector of the first surgical instrument, and when the first surgical instrument is positioned in a surgically prepared knee joint of the patient, the sensor contact is positioned in a predetermined location relative to an anatomical feature of the surgically prepared knee joint.

3. The system of claim 1, wherein when the sensor adapter is coupled to the sensor connector of the first surgical instrument, and when the first surgical instrument is positioned in a surgically prepared knee joint of the patient, the sensor contact is positioned in a predetermined compartment of the surgically prepared knee joint.

4. The system of claim 3, wherein the predetermined compartment comprises a medial compartment or a lateral compartment.

5. The system of claim 3, wherein the predetermined compartment comprises an anterior compartment or a posterior compartment.

6. The system of claim 1, wherein:
 the housing of the sensor adapter has a second surface positioned opposite the first surface, and a perimeter wall extending between the first surface and the second surface.

7. The system of claim 6, wherein the sensor contact has a predetermined location on the first surface relative to the perimeter wall.

8. The system of claim 6, wherein the sensor connector of each surgical instrument comprises:
 a locating feature positioned within the passageway, wherein the locating feature is configured to engage the perimeter wall of the sensor adapter.

9. The system of claim 8, wherein the first surgical instrument further includes a second inner wall extending inward from the outer wall into the passageway, the second inner wall configured to engage the second surface of the housing.

10. The system of claim 1, wherein the first surgical instrument of the plurality of surgical instruments comprises a shim block, and wherein the registering feature of the first surgical instrument comprises a lug hole defined through the shim block.

11. The system of claim 10, wherein the lug hole is configured to receive a lug of a gap assessment tool handle.

12. The system of claim 10, wherein the lug hole is configured to receive a lug of a tibial trial component.

13. The system of claim 1, wherein a first surgical instrument of the plurality of surgical instruments comprises a spacer base, and wherein the registering feature of the first surgical instrument comprises a tibial conforming surface configured to engage a surgically prepared tibia of the patient.

14. The system of claim 13, wherein the spacer base is attached to a spacer block of a gap assessment tool handle.

15. The system of claim 1, wherein a first surgical instrument of the plurality of surgical instruments comprises a surgical saw, and wherein the registering feature comprises a saw blade of the surgical saw.

16. The system of claim 1, wherein a first surgical instrument of the plurality of surgical instruments comprises a lamina spreader, and wherein the registering feature comprises a jaw of the lamina spreader.

17. The system of claim 1, wherein a first surgical instrument of the plurality of surgical instruments comprises a femoral sizer, and wherein the registering feature comprises a foot of the femoral sizer.

18. The system of claim 1, wherein a first surgical instrument of the plurality of surgical instruments comprises a femoral trial component, and wherein the registering feature comprises a bone-contacting surface of the femoral trial component.

19. The system of claim 1, wherein a first surgical instrument of the plurality of surgical instruments comprises a computer-assisted surgery tensioner, and wherein the registering feature comprises a bone-contacting surface of a distractor plate of the tensioner.

* * * * *